(12) United States Patent
Gleicher et al.

(10) Patent No.: US 8,629,120 B2
(45) Date of Patent: Jan. 14, 2014

(54) **METHOD OF TREATMENTS RELATED TO THE *FMR1* GENE**

(75) Inventors: Norbert Gleicher, Chicago, IL (US); David H Barad, Closter, NJ (US)

(73) Assignee: Women's Lab Company, LLC, Wilmington, DE (US)

( * ) Notice: Subject to any disclaimer, the term of this patent is extended or adjusted under 35 U.S.C. 154(b) by 91 days.

(21) Appl. No.: 13/612,566

(22) Filed: Sep. 12, 2012

(65) Prior Publication Data

US 2013/0012569 A1 Jan. 10, 2013

Related U.S. Application Data

(63) Continuation-in-part of application No. 13/360,349, filed on Jan. 27, 2012, and a continuation-in-part of application No. 13/043,199, filed on Mar. 8, 2011, and a continuation of application No. 12/508,295, filed on Jul. 23, 2009.

(51) Int. Cl.
*A61K 48/00* (2006.01)
*C12Q 1/68* (2006.01)
*C07H 21/04* (2006.01)
*C07H 21/02* (2006.01)

(52) U.S. Cl.
USPC ................ 514/44; 435/6; 536/23.1; 536/24.5

(58) Field of Classification Search
None
See application file for complete search history.

(56) References Cited

U.S. PATENT DOCUMENTS

| | | |
|---|---|---|
| RE39,920 E | 11/2007 | Umansky et al. |
| 2006/0177851 A1 | 8/2006 | Brennan et al. |
| 2009/0299645 A1 | 12/2009 | Colby et al. |
| 2011/0020795 A1 | 1/2011 | Gleicher et al. |
| 2013/0149297 A1* | 6/2013 | Bagni ........................ 424/130.1 |

OTHER PUBLICATIONS

Barad et al. Further Refinement in Defining the Effect of Heterozygous-abnormal CGG Counts on the FMR1 (Fragile X) Gene : Definition of a Distinct Subgroup of PCOS Patients, based on Normal/Low Genotype, Fertility and Sterility Abstract, Oct. 20, 2009, p. 59.
Gleicher et al. Can egg donor selection be improved?—A pilot study. Reproductive Biology and Endocrinology 2010, 8:76, http://www.rbej.com/content/8/1/76.
Gleicher, Norbert; FMR1 Genotype with Autoimmunity-Associated Polycystic Ovary-Like Phenotype and Decreased Pregnancy Chance Dec. 2010 | vol. 5 | Issue 12 | e15303.
Gleicher, Norbert, Can the FMR1 Gene Predict Early Ovarian Aging?, Women's Health, Mar. 2010, vol. 6, No. 2, pp. 165-169.
Gleicher, Norbert, Effects of Race/Ethnicity on Triple CGG counts in the FMR1 Gene in Infertile Women and Egg Donors, Reproductive Biomedicine Online 2010, vol. 20, pp. 485-491.
Gleicher, Norbert, Ovarian Reserve Determinations Suggest New Function of FMR1 (Fragile X Gene) in Regulating Ovarian Ageing, Reproductive Biomedicine Online 2010, vol. 20, pp. 768-775.
Gleicher, Norbert, The FMR1 Gene as Regulator of Ovarian Recruitment and Ovarian Reserve, Obstetrical & Gynecological Survey. Aug. 2010, 65(8) pp. 523-530.
Rotterdam ESHRE/ASRM-Sponsored PCOS Consensus Workshop Group 2004 (2004) Revised 2003 consensus on diagnostic criteria and long-term health risks related to polycystic ovary syndrome (PCOS). Hum Reprod 19: 41-47.
Fénichel P, Gobert B, Carré Y, Barbarino-Monnier P, Hiéronimus S (1999) Polycystic ovary syndrome in in autoimmune diseases. Lancet 353: 2210.
Van Gelderen CJ, Gomes dos Santos MI (1993) Polycystic ovarian syndrome. Evidence for an autoimmune mechanism in some cases. Journal of Reproductive Medicine 38: 381-386.
Hefler Frischmuth K, Walch K, Huebl W, Baummehlner K, Tempfer C, et al. (2010) Serologic markers of autoimmunity in women with polycystic ovary syndrome. Fertil Steril 93: 2291-2294.
Bannatyne P, Russell P, Shearman RP (1990) Autoimmune oophoritis: a clinic-pathologic assessment of 12 cases. Int J Gynecol Pathol 9: 191-207.
Londsdale RN, Roberts PF, Trowell JE (1991) Autoimmune oophoritis associated with polycystic ovaries. Histopathology 19: 77-81.
Ehrman DA (2005) Polycystic ovary syndrome. N Engl J Med 352: 1223-1236.
Hoek A, Schoemaker J, Drexhage HA (1997) Premature ovarian failure and ovarian autoimmunity. Endocr Rev 18: 107-134.
La Marca A, Marzotti S, Brozzetti A, Stabile G, Carducci Artenisio A, et al. on behalf of the Italian Addison Network. (2009) Primary ovarian insufficiency due to steroidogenic cell autoimmunity is associated with a preserved pool of functioning follicles. J Clin Endocrinol Metab 94: 3816-3823.
Oostra et al. FMR1: A gene with three faces Biochimica et Biophysica Acta 1790 (2009) 467-477.
Wall JR, Lahooti H (2010) Pathogenesis of thyroid eye disease—does autoimmunity against the TSH receptor explain all cases? Endocrynol Pol 61: 222-227.
Segars JH, DeCherney AH (2010) Is there a genetic basis for polycystic ovary syndrome. J Clin Endocrinol Metab 95: 2058-2060.
Dobrovic et al. DNA methylation, epimutations and cancer predisposition The International Journal of Biochemistry & Cell Biology 41 (2009) 34-39.
Gleicher N, Pratt D, Dudkiewicz A (1993) What do we really know about autoantibody abnormalities and reproductive failure: a critical review. Autoimmunity 16: 115-140.
Singh RR, Hahn BH, Tsao BP, Ebling FM (1998) Evidence for multiple mechanisms of polyclonal T cell activation in murine lupus. J Clin Invest 102: 1841-1849.
Sutmuller M, Baelde JJ, Madaio MP, Bruijn JA, De Heer E (1999) Idiotype usage by polyclonal activated B cells in experimental autoimmunity and infection. Clin Exp Immunol 115: 275-280.

*Primary Examiner* — Amy Bowman
(74) *Attorney, Agent, or Firm* — David W. Denenberg; Davidoff Hutcher & Citron LLP

(57) ABSTRACT

A method of treating a human to reduce the risk of malignancies or limit the spread of malignancies includes administering an FMR1 inhibitor to the human to block expression of an FMR1 gene. The FMR1 inhibitor blocks FMR1 genes in the human with at least one of two alleles with less than 26 triple CGG repeats.

24 Claims, 6 Drawing Sheets

(56) References Cited

OTHER PUBLICATIONS

Kim YJ, Ku SY, Jee BC, Suh CS, Kim SH, et al. (2010) A comparative study on the outcomes of in vitro fertilization between women with polycystic ovary syndrome and those with sonographic polycystic ovary-only in GnRH antagonist cycles. Arch Gynecol Obstet 2010.
Kuivasaari-Pirinen P, Hippelainen M, Hakkarainen H, Randell K, Heinonen S (2010) Cumulative baby take-home rate amongwomen with PCOS treated by IVF. Gynecol Endocrinol 2010.
Urman B, Tiras B, Yakin K (2004) Assisted reproduction in the treatment of polycystic ovarian syndrome. RBMOnline 8: 419-430.
Pessach IM, Notarangelo LD (2009) X-linked primary immunodeficiencies as a bridge to better understanding X-chromosome related autoimmunity. J Autoimmunity 33: 17-24.
Larizza D, Calcaterra V, Martinet M (2009) Autoimmune stigmata in Turner syndrome: When lacks an X chromosome. J Autoimmunity 33: 25-30.
Bilousova TV, Dansie L, Ngo M, et al. Minocyline promotes dendritic spine maturation and improves behavioural performance in the fragile x mouse model. J Med Genet 2009;46:94-102.
Persani L, Rossetti R, Cacciatore C, Bonomi M (2009) Primary ovarian insufficiency: X chromosome defects and autoimmunity. J Autoimmunity 33: 35-41.
Marozzi A, Manfredini E, Tibiletti MG, Furlan D, Villa N, et al. (2000) Molecular definition of Xq common-deleted region in patients affected by premature ovarian failure. Hum Genet 107: 304-311.
Cremer FP, van de Pol DJ, Diergaarde PJ, Wieringa B, Nussbaum RL, et al. (1989) Physical fine mapping of the choroideremia locus using Xq21 deletions associated with complex syndromes. Genomics 4: 41-46.
Pepper AS, Beerman RW, Bhogal B, et al. Argonuate2 supresses Drosophilia fragile x expression preventing neurogenesis and oogenesis defects. PLoS One 2009;4:e7618.
Gleicher N, Weghofer A, Oktay K, Barad D (2009) Do etiologies of premature ovarian aging (POA) mimic those of premature ovarian failure (POF)? Hum Reprod 24: 2395-2400.
Aziz R (2006) Diagnosis of polycystic ovarian syndrome: The Rotterdam Criteria are premature. J Clin Endocrinol Metab 91: 781-785.
Ott J, Aust S, Kurz C, Nouri K, Wirth S, et al. (2010) Elevate antithyroid peroxidase antibodies indicating Hashimoto's thyroiditis are associated with treatment response in infertile women with polycystic ovary syndrome. Fertil Steril;. In press.
Baroni SS, Santillo M, Bavilacqua F, Luchetti M, Spadoni T, et al. (2006) Stimulating autoantibodies to the PDGF receptor in systemic sclerosis. N Engl J Med 354: 2667-2676.
Wagner, T., et al., (1999), "Denaturing High-Performance Liquid Chromatography Detects Reliably BRCA1 and BRCA2 Mutations", Genomics, vol. 62, Issue 3, pp. 369-376.
Sanger, F., Nicklen, S., Coulson, R. (1977), "DNA Sequencing with Chain-Terminating Inhibitors", Pros. Natl Acad Sci USA, V.74 (12) pp. 5463-5467.
Petek, E., et al., (1999), "Mosaicism in a Fragile X Male Including a De Novo Deletion in the FMR1 gene", Am. J. Med. Genet., vol. 84, Issue 3, pp. 229-232.
Gleicher, N., et al., (2010), "Ovarian reserve determinations suggest new function of FMR1 (fragile X gene) in regulating ovarian ageing", Reprod. Biomed Online, 20(6), pp. 768-775.
Gleicher, N., et al., (2010) "FMR1 Genotypes with Autoimmunity-Associated Polycystic Ovary-Like Phnotype and Decreased Pregnancy Chance", PLoS ONE 5(12) e15303.
Gleicher, N., et al. (2010), "Association of FMR1 Genotypes with In Vitro Fertilization (IVF) Outcomes Based on Ethnicity/Race", PLoS ONE 6(4): e18781. doi:10.1371/journal.pone.0018781.
Oktay, K., et al., (2010), "Association of BRCA1 Mutations with Occult Primary Ovarian Insufficiency: A Possible Explanation for the Link between Infertility and Breast/Ovarian Cancer Risks", J Clin Oncol, 28 (2):pp. 240-244.
Gleicher, N., et al., (2009), "Correlation of Triple Repeats on the FMR1 (fragile X) Gene to Ovarian Reserve: A New Fertility Test?", Acta Obstet Gynecol Scand 2009;88(9); pp. 1024-1030.
Evers, B., et al., (2006), "Mouse Models of BRCA1 and BRCA2 deficiency; past lessons, current understanding and future prospects", Oncogene, 25, 5885-5887, doi:10.1038/sj.onc.1209871.
Crook T, Crossland S, Crompton MR, Osin P, Gusterson BA. P53 Mutation in BRCA1-Associated Family Breast Cancer. Lancet 1997;350:638-9.
Xu, C.-F., et al., (1997), "Mutations and alternative splicing of the BRCA1 gene in UK breast/ovarian cancer families." Genes, Chromosomes and Cancer, 18: 102-110. doi: 10.1002/(SICI)1098-2264(199702)18:2<102::AID-GCC4>3.0.CO;2-6.
Cao, L., et al., (2003) "Senescence, aging, and malignant transformation mediated by p53 in mice lacking the BRCA1 full-length isoform", Genes & Development, 17, pp. 201-213.
Hakem, R., et al., (1997) "Partial Rescue of BRCA1 (5-6) Early Embryonic Lethality by p53 or p21 null mutation", Nat. Genet., (3) 298-302.
Ludwig, T., et al., (1997) "Targeted mutations of breast cancer susceptibility gene homologs in mice: lethal phenotypes of Brca1, Brca2, Brca1/Brca2, Brca1/p53, and Brca2/p53 nullizygous embryos.", Genes Dev. 1997 11, pp. 1226-1241.
Willemsen, R., et al., (2011) "CGG repeat in the FMR1 gene: size matters", Clinical Genetics, vol. 80, Issue 3, pp. 214-225.
Nelson, L.M., (2009) "Primary Ovarian Insufficiency", New England Journal of Medicine, 360(6), pp. 606-614.
Chen, L.S., et al., (2003) "The (CGC)n repeat element within the 5' untranslated region of the FMR1 message provides both positive and negative cis effects on in vivo translation of a downstream reporter", Human Molecular Genetics, 2003, vol. 23, No. 23, pp. 3067-3074.
Gleicher N, Barad DH (2007) "Gender as risk factor for autoimmune diseases." J Autoimmunity 28: 1-6.
Gleicher, N., et al., "Cutting edge assessment of the impact of autoimmunity on female reproductive success", J Autoimmun doi:10.1016/j.jaut.2011.05.016 (2011).
Altekruse, S.F., et al., SEER Cancer Statistics Review 1975-2007, Bethesda, MD, National Cancer Institute (2010).
Campeau, P.M., et al., "Hereditary breast cancer: new genetic developments, new therapeutic avenues", Human Genetics, 124(1):31-42 (2008).
Kadouri, L., et al., "Cancer risks in carriers of the BRCA 1/2 Ashkenazi founder mutations", J. Med. Genet., 44.467 (2007).
Thomson, D., et al., Cancer Incidence in BRCA1 Mutation Carriers, Journal of the National Cancer Institute, vol. 94, No. 18, Sep. 18, 2002.
The Breast Cancer Linkage Consortium, "Cancer Risks in BRCA2 Mutation Carriers", Journal of the National Cancer Institute, vol. 91, No. 15, Aug. 4, 1999.
Antoniou, A.C., et al., (2001) "Evidence for further breast cancer susceptibility genes in addition to BRCA1 and BRCA2 in a population-based study", Genetic Epidemiology, 21:1-18. doi: 10.1002/gepi.1014.
John, E.M., et al., "Prevalence of Pathogenic BRCA1 Mutation Carriers in 5 US Racial/Ethnic Groups", JAMA. 2007; 298(24):2869-2876. doi:10.1001/JAMA.294.24.2869.
Vogel, K.J., et al. "BRCA1 and BRCA2 Genetic Testing in Hispanic Patients: Mutation Prevalence and Evaluation of the BRCAPRO Risk Assessment Model", JCO 2007; 25(29); 4635-4641. doi:10.1200/JCO.2006.10.4703.
Malone, K.E., et al., :Prevalence and Predictors of BRCA1 and BRCA2 Mutations in a Population-Based Study of Breast Cancer in White and Black American Women Ages 35 to 64 Years, Cancer Res., 2006 66; 8297. doi: 10.1158/0008-5472.CAN-06-0503.
Ademuyiwa, F.O., et al., "Breast cancer racial disparities: unanswered questions", Cancer Res., Feb. 1, 2011;71(3) 640-4.
Terplan, M., et al., "Have racial disparities in ovarian cancer increased over time? An analysis of SEER data", Gynecol Oncol, Nov. 21, 2011. [Epub ahead of print].
Ikeami, J., et al. "Genetics of type 1 diabetes in Asian and Caucasian populations", Diabetes Research and Clinical Practice, vol. 77, Issue 3, Supplement, pp. S116-S121, Sep. 2007.
Aerts JM, Bols PE. Ovarian follicular dynamics: a review with emphasis on the bovine species. Part I: Folliculogenesis and preantral follicle development. Reprod Domest Anim 2010;45:171-9.

(56) References Cited

OTHER PUBLICATIONS

Dumesic DA, Abbott DH. Implications of polycystic ovary syndrome on oocyte development. Semin Reprod Med 2008;26:53-61.

Gleicher N, Weghofer A, Barad DH. The role of androgens in follicle maturation and ovulation induction: friend or foe of infertility treatment? Reprod Biol Endocrinol 2011;9:116.

Li M, Schatten H, Sun QY. Androgen receptor's destiny in mammalian oocytes: a new hypothesis. Mol Hum Reprod 2009;15:149-54.

Lenie S, Smitz J. Functional AR signaling is evident in an in vitro mouse follicle culture bioassay that encompasses most stages of folliculogenesis. Biol Reprod 2009;80:685-95.

Barad D, Gleicher N. Effect of dehydroepiandrosterone on oocyte and embryo yields, embryo grade and cell number in IVF. Hum Reprod 2006;21:2845-9.

Barad D, Brill H, Gleicher N. Update on the use of dehydroepiandrosterone supplementation among women with diminished ovarian function. J Assist Reprod Genet 2007;24:629-34.

Gleicher N, Ryan E, Weghofer A, Blanco-Mejia S, Barad DH. Miscarriage rates after dehydroepiandrosterone (DHEA) supplementation in women with diminished ovarian reserve: a case control study. Reprod Biol Endocrinol 2009;7:108.

Gleicher N, Weghofer A, Barad DH. Dehydroepiandrosterone (DHEA) reduces embryo aneuploidy: direct evidence from preimplantation genetic screening (PGS). Reprod Biol Endocrinol 2010;8:140.

Casson PR, Lindsay MS, Pisarska MD, Carson SA, Buster JE. Dehydroepiandrosterone supplementation augments ovarian stimulation in poor responders: a case series. Hum Reprod 2000;15:2129-32.

Genazzani AR, Stomati M, Valentino V, et al. Effect of 1-year, low-dose DHEA therapy on climacteric symptoms and female sexuality. Climacteric 2011;14:661-8.

Gleicher N, Weghofer A, Barad DH. Improvement in diminished ovarian reserve after dehydroepiandrosterone supplementation. Reprod Biomed Online 2011;21:360-5.

Gleicher N, Weghofer A, Barad DH. Discordances between follicle stimulating hormone (FSH) and anti-Mullerian hormone (AMH) in female infertility. Reprod Biol Endocrinol 2010;8:64.

Sullivan SD, Castrillon DH. Insights into primary ovarian insufficiency through genetically engineered mouse models. Semin Reprod Med 2011;29:283-98.

Barad DH, Weghofer A, Gleicher N. Age-specific levels for basal follicle-stimulating hormone assessment of ovarian function. Obstet Gynecol 2007;109:1404-10.

Barad DH, Weghofer A, Gleicher N. Utility of age-specific serum anti-Mullerian hormone concentrations. Reprod Biomed Online 2011;22:284-91.

Barad DH, Gleicher N. Increased oocyte production after treatment with dehydroepiandrosterone. Fertil Steril 2005;84:756.

Monget P, Bobe J, Gougeon A, Fabre S, Monniaux D, Dalbies-Tran R. The ovarian reserve in mammals: A functional and evolutionary perspective. Mol Cell Endocrinol 2011.

Center for Devices and Radiological Health (CDRH), U.S. Food and Drug Administration: Electronic Human Cell and Tissue Establishment Registration (eHCTERS). [http://www.fda.gov/cber/tissue/tisreg.htm].

Kodama H, Fukuda J, Karube H, Matsui T, Shimizu Y, Tanaka T: High incidence of embryo transfer cancellations in patients with polycystic ovarian syndrome. Hum Reprod 1995, 10:1962-1967.

Tummon I, Gavrilova-Jordan L, Allemand MC, Session D: Polycystic ovaries and ovarian hyperstimulation syndrome: a systematic review. Acta Obstet Gynecol Scand 2005, 84:611-616.

Gnoth C, Schuring AN, Friol K, Tiggens J, Mallmann P, Godehardt E: Relevance of anti-Müllerian hormone measurement in routine IVF program. Hum Reprod 2008, 23:1359-1365.

Nelson SM, Yates RW, Lyall H, Maybeth J, Traynor I, Gaudion M, Mitchell P, Ambrose P, Fleming R: Anti-Müllerian hormone-based approach to controlled ovarian stimulation for assisted conception, Hum Reprod 2009, 24:867-875.

Carlsen SM, Vanky E, Fleming R: Anti-Müllerian hormone concentrations in androgen-suppressed women with polycystic ovary syndrome. Hum Reprod 2009, 24:1732-1738.

Gleicher N, Weghofer A, Oktay K, Barad DH: The FMR1 (fragile X) gene serves as predictor of response to ovarian stimulation. Reprod Sciences 2009, 16:462-467.

Epstein Am, Bauer CA, Ho A, et al. Drosophila Fragile x protein controls cellular proliferation by regulating cbl levels in the ovary. Dev Biol 2009;330:89-92.

Kevenaar ME, Meerasahib MF, Kramer P, van de Lang-Born MBN, de Jong FH, Groome NP, Themmen APN, Visser JA: Serum AMH levels reflect the size of the primordial follicle pool in mice. Endocrinology 2006, 147:3228-3224.

Ebner T, Sommergruber M, Moser M, Shebl O, Schreier-Lechner E, Tews G: Basal level of anti-Müllerian hormone is associated with oocytes quality in stimulated cycles. Hum Reprod 2006, 21:2022-2026.

Fleming R, Deshpande N, Traynor I, Yates RW: Dynamics of FSH-induced follicular gowth in subfertile women: relationship with age, insulin resistance, oocytes yield and anti-Mullerian hormone. Hum Reprod 2006, 21:1436-41.

Sun W, Stegman BJ, Henne M, Catherino WH, Segars JH: A new approach towards ovarian reserve testing. Fertil Steril 2008, 90:2196-2203.

Broer SL, Mol BWJ, Hendriks D, Broekmans FJM: The role of antimullerian hormone in predicting outcome after IVF: comparison with antral follicle count. Fertil Steril 2009, 91:705-715.

Knauff EA, Eijkemans MJ, Lambalk CB, ten Kate-Booji MJ, the Dutch Premature Ovarian Failue Consortium, et al.: Anti-Müllerian hormone, inhibin B, and antral follicle count in young women with ovarian failure. J Clin Endocrinol Metab 2009, 94:786-792.

Nelson SM, Yates RW, Fleming R: Serum anti-Müllerian hormone and FSH: prediction of live birth and extremes of response in stimulation cycles-implications for individualization of therapy. Hum Reprod 2007, 22:2414-2421.

Toner JP: Modest follicle-stimulating hormone elevations in younger women: wyarn but don't disqualify. Fertil Steril 2004, 81:1493-1495.

Murray, A., Ennis, S., MacSwiney, F., Webb, J., Morton, N.E, 2000. Reproductive and menstrual history of females with fragile X expansions. Eur. J. Hum. Genet. 8, 247-252.

Rohr, J., Allen, E.G., Charen, K., et al., 2008. Anti-Mullerian hormone indicates early ovarian decline in fragile x mental regardation (FMR1) permutation carriers: a preliminary study. Hum. Reprod. 23, 1220-1225.

Crawford, D.C., Acuna, J.M., Sherman, S.L., 2001. FMR1 and the fragile x syndrome: human genome epidemiology review. Genet. Med. 3, 359-371.

Crawford, D.C., Meadows, K.L., Newman, J.L., et al., 2002. Prevalence of the fragile x syndrome in African Americans. Am. J. Med. Genet. 3, 359-371.

Gleicher, N., Weghofer, A., Li, J.M., Barad, D., 2007 Differences in ovarian function parameters between Chinese and Caucasian oocyte donors: do they offer an explanation for lower IVF pregnancy rates in Chinese Women? Hum. Reprod. 22, 2879-2882.

Yang Y, Xu S, Xia L, et al. The bantam microRNA is associated with drosophila fragile x mental retardation protein and regulates the fate of germline stem cells. Plos Genet 2009;5:31000444.

Van Disseldorp J. Faddy MJ, Themmen AP., et al., Relationship of serum antimullerian hormone concentration to age at menopause. J. Clin. Endocrinol. Metab. 93, 2219-2134 (2008).

Hagerman RJ, Hagerman PJ. Testing for fragile x mutations throughout the life span. JAMA 2008; 300: 2419-2421.

Verheij C, Bakker CA, de Graaff E. et al. Characterization and localization of the FMR-1 gene product associated with fragile x syndrome. Nature 1993: 363: 722-724.

Bassel GJ, Warren ST. Fragile X syndrome: loss of local mRNA regulation after synaptic development and function. Neuron 2008; 60: 201-214.

Ashley CT, Sutcliffe JS, Kunst CB, et al. Human and murie FMR-1: alternative splicing and translation initiation downstream of the CGG-repeat. Nat Genet 1993; 4: 244-251.

Wilson JA, Pratt VM, Phansalkar A, et al; the FragileXperts Working Group of the Association for Molecular Pathology Clinical Practice

(56) References Cited

OTHER PUBLICATIONS

Committee 2008. Consensus characterization of 16 FMR1 reference materials: a consortium study. J Molec Diagnost 10:2-12.
Oberle I, Russeau F, heits D, et al. Instability of a 55-base pair DNA segment and abnormal methylation in fragile x syndrome. Science 1991: 252: 1097-1102.
Naumann A, Hochestein N, Weber S, et al. A distinct DNA-methylation boundary in the 5'-upstream sequence of the FMR1 promoter binds nuclear proteins and is lost in fragile X syndrome. AM J Hum Genet 2009;85:606-616.
Allen EG, He W, Yadav-Shah M, et al. A study of the distribution characteristics of the FMR1 transcript levels in 238 individuals. Hum Genet 2004;114:439-447.
Hunter JE, Rohr JK, Sherman SL. Co-occuring diagnosis among FMR1 premutation allele carriers. Clin Genet 2010;77:374-381.
Berman RF, Willemsen R. Mouse models of fragile x-associated tremor/ataxia syndrome. J investig Med 2009; 57:737-741.
Brouwer JR, Willemsen R, Oostra BA. The FMR1 gene and fragile x-associated tremor/ataxia syndrome. Am J Med Genet B Neuropsychiatr Genet 2009; 150B:782-798.
Garcia-Alegria E, Ianez B, Minguez M, et al. Analysis of FMR1 gene expression in female premutation carriers using robust segmented linear regression models. RNA 2007;113:756-762.
Minguez M, Ibanez B, Ribate MP, et al. Risk of cognitive impairment in female premutation carriers of fragile x premutation: analysis by means of robust segmented linear regression model. Am J Med Genet B Neuropsychiatr Genet 2009;150B:262-270.
Tassone F, Hagermann PJ. Expression of the FMR1 gene. Cytogenet Genome Res 2003;100:124-128.
Peprah E, He W, Allen E, et al. Examination of the FMR1 transcript and protein levels among premutation carriers. J Hum Genet 2009;55:66-68.
Coffey SM, Cook K, Tartaglia N, et al. Expanded clinical phenotype of women with the FMR1 premutation. AM J Med Genet 2008;146A: 1009-1016.
Hunter JE, Epstein MP, Tinker SW, et al. Fragile X-associated primary ovarian insufficiency: evidence for additional genet contributions to severity. Genet Epidemiol 2008;32:553-559.
Tejada MI, Garcia-Alegria E, Bilbao A, et al. Analysis of the molecular parameters that could predict the risk of manifesting premature ovarian failure in female premutation carriers of fragile x syndrome. Menopause 2008;15:945-949.
Chatterjee S, Maitra A, Kadam S, et al. CGG repeat sizing in the FMR1 gene in Indian women with premature ovarian failure. Reprod Biomed Online 2009;19:281-286.
Gleicher N, Weghofer A, Barad DH. Ovarian reserve determinations suggest new function of FMR1 (fragile x) gene in regulating ovarian aging. Reprod Biomed Online 2010;20:768-775.
Durlinger AL, Visser JA, Themmen AP. Regulation of ovarian function: the role of anti-Mullerian hormone. Reproduction 2002;124:601-609.
Gleicher N, Weghofer A, Barad D. Too old for IVF: are we discriminating against older women? J Assist Reprod Genet 2007;24:639-644.
Kalberer U, Baud D, Fontanet A, et al. Birth records from Swiss married couples analyzed over the past 35 years reveal an aging of first-time mothers by 5.1 years while the interpregnancy interval has shortened. Fertil Steril 2009;92:2072-2073.
Hergersberg M, Matsuo K, Gassmann M, et al. Tissue-specific expression of FMR1/beta-galactosidase fusion gene in transgenic mice. Hum Molec Genet 1995;4:359-366.
Yang L, Duan R, Chen D, et al. Fragile X mental retardation protein modulates fate of germline stem cells in drosophila. Hum Mol Genet 2007;16:1814-1820.
Gosden RG, Treloar SA, Martin NG, Cherkas LF, Spector TD, Faddy MJ, Silber SJ. Prevalence of premature ovarian failure in monozygotic and dizygotic twins. Human Reproduction (2007) 22:610-615.
Goswami R, Marwaha RK, Goswami D, Gupta N, Ray D, Tomar N, Singh S. Prevalence of thyroid autoimmunity in sporadic idiopathic hypoparathyroidism in comparison to type 1 diabetes and premature ovarian failure. Journal for Clinical Endocrinology Metabolism (2006) 91:4256-4259.
Hoek A, Schoemaker J, Drexhage HA. Premature ovarian failure and ovarian autoimmunity. Endocrinology Revised (1997) 18:107-134.
Kovanci E, Rohozinski J, Simpson JL, Heard MJ, Bishop CE, Carson SA. Growth differentiating factor-9 mutation may be associated with premature ovarian failure. Fertility and Sterility (2007) 87:143-146.
Machado-Ferreira Mdo C, Costa-Lima MA, Boy RT, Esteves GS, Pimentel MM. Premature ovarian failure and FRAXA permutation: positive correlation in a Brazilian survey. American Journal of Medical Genetics (2004) 126A:237-240.
Miano MG, Leperuta C, Chiurazzi P, D'Urso M, Ursini MV. Ovarian dysfunction and FMR1 alleles in a large Italian family with POF and FRAXA disorders: case report. BMC Medical Genetics (2007) 8:18.
Nikolaou D, Templeton A. Early ovarian ageing: a hypothesis. Detection and clinical relevance. Human Reproduction (2003) 18:1137-1139.
Barad D, Gleicher N. Effect of dehydroepiandrosterone on oocyte and embryo yields, embryo grade and cell number in IVF. Hum Rprod 2006;21:2845-9.
Qin Y, Choi Y, Zhao H, Sipson JL, Chen ZJ, Rajkovic. A. NOBOX homeobox mutation causes premature ovarian failure. American Journal of Human Genetics (2007) 81:576-581.
Rajareddy S, Reddy P, Du C, Liu L, Jagarlamudi K, Tang W, Shen Y, Berthet C, Peng SL, Kaldis P, et al. p27kip1 (cyclin-dependent kinase inhibitor 1B) controls ovarian development by suppressing follicle endowment and activation and promoting follicle atresia in mice. Molecular Endocrinology (2007) 21:2189-2202.
Reddy P, Liu A, Adhikari D, Jagarlamudi K, Rajareddy S, Shen Y, Du C, Tang W, Hamalainen T, Tang SL, et al. Oocyte-specific deletion of Pten causes premature activation of the primordial follicle pool. Science (2008) 319:611-613.
Barad D, Brill H, Gleicher N. Update on the use of dehydroepiandrosterone supplementation among women with diminished ovarian function. J Assist Reproduction Genet 2007; 24: 629-34.
Gleicher N, Barad D. Unexplained infertility: Does it really exist? Hum Reprod 2006;21:1951-6.
Streuli I, Fraisse T, Ibecheole V, Moix I, Morris MA, de Ziegler D. Intermediate and permutation FMR1 alleles in women with occult primary ovarian insufficiency. Fertility and Sterility (2008) 92 (2): 464-70.
Sundblad V, Bussman L, Chiauzzi VA, Pancholi V, Charreau EH. Alpha-enolase: a novel autoantigen inpatients with premature ovarian failure. Clinical Endocrinology (Oxf) (2006) 65:745-751.
Takamizawa S, Shibahara H, Shibayama T, Suzuki M. Detection of antizona pellucida antibodies in the sera from premature ovarian failure patients by a highly specific test. Fertility and Sterility (2007) 88:925-932.
Nelson JL, Koepsell TD, Dugowson CE, Voigt LF, Daling JR, Hansen JA. Fecundity before disease onset in women with rheumatoid arthritis. Arthritis Rheum 1993;36:7-14.
Vegetti W, Marozzi A, Manfredini E, Testa G, Alagna F, Nicolosi A, Caliari I, Taborelli M, Tibiletti MG, Dalpra L, et al. Premature ovarian failure. Molecular Cell Endocrinology (2000) 161:53-57.
Welt CK. Primary ovarian insufficiency: a more accurate term for premature ovarian failure. Clinical Endocrinology (Oxf) (2008) 68:499-509.
Arbuckle MR, McClain MT, Rubertone MV, Scofield RH, Dennis GJ, James JA, et al. Development of autoantibodies before the clinical onset of systemic lupus erythematosus. N Engl J Med 2003;349:1526-33.
Shmerling RH. Autoantibodies in systemic lupus erythematosus—there before you know it. N Engl J Med 2003; 349:1499-500.
McConkie-Rosell A, Finucane B, Cronister A, Abrams L, Bennett RL, Pettersen BJ. Genetic counseling for fragile x syndrome: updated recommendations of the national society of genetic counselors. J Genet Couns 2005;14:249-70.
McConkie-Rosell A, Abrams L, Finucane B, Cronister A, Gane LW, Coffey SM, Sherman S, Nelson LM, Berry-Kravis E, Hessl D, Chiu S, Street N, Vatave A, Hagerman RJ. Recommendations from multi-

(56) References Cited

OTHER PUBLICATIONS disciplinary focus groups on cascade testing and genetic counseling for fragile X-associated disorders. Journal of Genetics Counsel 2007; 16:593-606.

Luborsky JL, Meyer P, Sowers MF, Gold EB, Santoro N. Premature menopause in multi-ethnic population study of the menopause transition. Human Reproduction 2003; 18: 199-206.

Aoki K, Dudkiewicz AB, Matsuura E, Novotny M, Kaberlein G, Gleicher N. Clinical significance of beta 2-glycoprotein I-dependent anticardiolipin antibodies in the reproductive autoimmune failure syndrome: correlation with conventional antiphospholipid antibody detection systems. Am J Obstet Gynecol 1995;172:926-31.

Welt CK, Smith PC, Taylor AE. Evidence of early ovarian aging in fragile X premutation carriers. Journal for Clinical Endocrinology Metabolism 2004; 89:4569-74.

Pluzhnikov A, Nolan DK, Tan Z, McPeek MS, Ober C 2007 Correlation of intergenerational family sizes suggests a genetic component of reproductive fitness. Am J Hum Genet 81,165-9.

Gleicher N, Weghofer A, Oktay K, Barad DH. Is the immunological noise of abnormal autoimmunity an independent risk factor for premature ovarian aging? Menopause; In press; (manuscript available upon request).

Gleicher N, Weghofer A, Oktay K, Barad DH. Correlation of triple repeats on the FMR1 (fragile X) gene to ovarian reserve: A new infertility test? Submitted for publication; (manuscript available upon request).

Fragile X-Primary Ovarian Insufficiency (FX-POI) Working Group 2008 http://www.ncbi.nlm.nih.gov/pubmed/18357616.

Barad DH, Weghofer A, Gleicher N. Comparing anti-Mullerian (AMH) and follicle stimulating (FSH) hormones as predictors of ovarian function. Fertility and Sterility; 2009; 91:1553-5.

Hill GA, Scott RJ, Jr. Immunologic tests and IVF: please enough already. Fertility and Sterility 2000; 74: 439-42.

Practice Coomittee of the American Society for Reproductive Medicine; Practice Committee of the Society for Assisted Reproductive Technology 2006; Guidelines for Gamete and Embryo Donation. Fertility and Sterility 2006; 86:S38-50.

Lorusso F, Vicino M, Lamanna G, Trerotoli P, Serio G, Depalo R Performance of different ovarian reserve markers for predicting numbers of ocytes retrieved and mature oocytes. Maturitas 2007; 56:429-35.

Nikolaou D, Templeton A. Early ovarian ageing. 2004 European Journal for Obstetrics and Gynecology and Reproductive; Biol 113:126-33.

Hornstein MD. Antiphospholipid antibodies in patients undergoing IVF: the data do not support testing. Fertility and Sterility 2000; 74: 635-6.

Gleicher N, Vidali A, Karande V. The immunological "Wars of the Roses": disagreements amongst reproductive immunologists. Human Reproduction 2002; 17: 539-42.

Gleicher N, Friberg J. IgM gammopathy and the lupus anticoagulant syndrome in habitual aborters. JAMA 1985; 253: 3278-81.

Rombauts L. Is there a recommended maximum starting dose of FSH in IVF? J Assist Reprod Genet 2007;24:343-9.

Purcell K, Schembri M, Frazier LM, Rall MJ, Shen S, Croughan M, Grainger DA, Fujimotoa VY 2007 Asian ethnicity is associated with reduced pregnancy outcomes after assisted reproductive technology. Fertil Steril 87, 297-302.

Saluto, et al., "An enhanced polymerase chain reaction assay to detect pre- and full mutation alleles of the Fragile X Mental Retardation 1 Gene," Journal of Molecular Diagnostics, vol. 7, No. 5, Nov. 2005, pp. 605-612.

Sullivan, et al., "Association of FMR1 repeat size with ovarian dysfunction," Human Reproduction, 2005, vol. 20, No. 2, pp. 402-412.

Yan, et al., "Identificaiton of premature ovarian failure patients with underlying autoimmunity," J Womens Health Gend Based Med, 2000, vol. 9, No. 3, pp. 275-287.

Knauf, E., "POF: from phenotype to genotype (general introduction)," Premature ovarian failure from phenotype to genotype (online) Amsterdam, Utrecht University, Apr. 22, 2009 (retrieved on Aug. 29, 2010), retrieved from the internet: http://igitur-archive.library.uu.nl/dissertations/2009-0806-200142/knauff.pdf, ISBN 978 903 935 0263, pp. 1-144.

Broekmans, et al., "Female reproductive ageing: current knowledge and future trends," Trends in Endocrinology and Metabolism, vol. 18, No. 2, Feb. 1, 2007.

Gleicher, et al., "Relevance of triple CGG repeats in the FMR1 gene to ovarian reserve," Reproductive Biomedicine Online, Jul. 23, 2009, vol. 19, Issue 3, pp. 385-390.

International Searching Authority (ISA/US), International Search Report for International Patent Application PCT/US10/43034, International Filing Date Jul. 23, 2010, ISR date of mailing Nov. 15, 2010, 2 pages.

Gleicher N. Weghofer A. Barad DH. A pilot study of premature ovarian senescence: I correlation of triple CGG repeats on the FMR1 gene to ovarian reserve parameters FSH and anti-Mullerian hormone. Fertile Steril 2009; 91; 1700-6.

Sen A. Hammes SR. Granulosa cell-specific androgen receptors are critical regulators of ovarian development and function. Mol Endocrinol 2010;24: 1393-403.

Wiser A, Gonen 0, Ghetler Y, Shavlt T, Berkovitz A, Shulman A. Addition of dehydroeplandrosterone (DHEA) for poor-responder patients before and during IVF treatment Improves the pregnancy rate: a randomized prospective study, Hum Reprod 2010;25:2496-500.

Frattareill JL, Peterson EH, Effect of androgen levels on in vitro fertilization cycles. Fertil Steril 2004;81:1713-4.

Massin N, Cedrin-Dumerin I, Coussieu C, Galey-Fontaine J, Wolf JP, Hugues JN, Effects of transdermal testosterone application on the ovarian response to FSH in poor responders undergoing assisted reproduction technique—a prospective, randomized, double-blind study, Hum Reprod 2006;21:1204-11.

Blbl G, Malcov M, Yuval Y, et al. The effect of CGG repeat number on ovarian response among fragile X premutatlon carriers undergoing preimplantation genetic diagnosis, Fertil Steril 2010;94:869-74.

Qin Y, Zhao Z, Sun M, Geng L, Che L, Chen ZJ, Association of basal serum testosterone levels with ovarian response and in vitro fertilization outcome. Reprod Biol Endocrinol 2011;9:9.

Weghofer A, Glelcher N. Ovarian function: a theory of relativity. Hum Reprod 2009;24;17-9.

Fortune JE. The early stages of follicular develepment: activation of primordial follicles and growth of preantral follicles Anim Reprod Sci 2003;78:135-63.

Nielsen ME, Rasmussen IA, Kristensen SG, et al. In human granulosa cells from small antral follicles, androgen receptor mRNA and androgen levels in follicular fluid correlate with FSH receptor mRNA. Mol Hum Reprod 2011;17:63-70.

Well SJ, Vendola K, Zhou J, et al, Androgen receptor gene expression in the primate ovary: cellular localization, regulation, and functional correlations. J Clin Endocrinol Metab 1998;83:2479-85.

Well S, Vendola K, Zhou J, Bondy CA. Androgen and follicle-stimulating hormone interactions in primate ovarian follicle development. J Clin Endocrinol Metab 1999;84:2951-6.

Casson PR, Kristiansen SB, Umstot E, Carson SA, Buster JE. Ovanan hyperstimulation augments adrenal dehydroepiandrosterone sulfate secretion. Fertil Steril 1996;65:950-3.

Heijnen EM, Eijkemans MJ, Hughes EG, Laven JS, Macklon NS, Fauser BC. A meta-analysis of outcomes of conventional IVF in women with polycystic ovary syndrome. Hum Reprod Update 2006;12:13-21.

Armstrong DG, Gutierrez CG, Baxter G, et al. Expression of mRNA encoding IGF-I, IGF-II and type 1 IGF receptor in bovine ovarian follicles. J Endocrinol 2000;165:101-13.

Baker J, Hardy MP, Zhou J, et al. Effects of an Igf1 gene null mutation on mouse reproduction. Mol Endocrinol 1996;10:903-18.

Zhou J, Kumar TR, Matzuk MM, Bondy C. Insulin-like growth factor I regulates gonadotropin responsiveness in the murine ovary. Mol Endocrinol 1997;11:1924-33.

Hodges CA. Ilagan A, Jennings D, Keri R, Nilson J, Hunt PA. Experimental evidence that changes in oocyte growth influence meiotic chromosome segregation. Hum Reprod 2002;17:1171-80.

(56) References Cited

OTHER PUBLICATIONS

Kroon S, Harrison K, Martin N, Wong B, Yazdani A. Miscarriage karyotype and Its relationship with maternal body mass index, age, and mode of conception. Fertil Steril 2011;95:1827-9.

Dewailly D, Pigny P, Soudan B, et al. Reconciling the definitions of polycystic ovary syndrome: ovarian follicle number and serum anti-Mullerian hormone concentrations aggregate with the markers of hyperandrogenism. J Clin Endocrinol Metab 2010;95:4399-405.

Allen EG, Sullivan AK, Marcus M et al. 2007 Examination of reproductive aging milestones among women who carry the FMR1 premutation. Human Reproduction (2007) 22, 2142-2152.

Bächner D, Steinbach P, Wöhrle D et al. 1993a Enhanced Fmr-1 expression in testis. Nature Genetics 4, 115-116.

Bächner D, Manca A, Steinbach P et al. 1993b Enhanced expression of the murine FMR1 gene during germ cell proliferation suggests a special function in both the male and the female gonad. Human Molecular Genetics 2, 2043-2050.

Barad DH, Weghofer A, Gleicher N 2007 Age-specific levels for basal follicle-stimulating hormone assessment of ovarian function. Obstetrics and Gynecology 109, 1404-1410.

Bodega B, Bione S, Dalpra L et al. 2006 Influence of intermediate and uninterrupted FMR1 CGG expansions in premature ovarian failure manifestation. Human Reproduction 21, 952-957.

Bretherick KL, Fluker MR, Robinson WP 2005 FMR1 repeat sizes in the gray zone and high end of the normal range are associated with premature ovarian failure. Human Genetics 117, 376-382.

Chen MJ, Yang WS, Chen CL et al. 2008 The relationship between anti-Mullerian hormone, androgen and insulin resistance on the number of antral follicles in women with polycystic ovary syndrome. Human Reproduction 23, 952-957.

Chen LS, Tassone F, Sahota P, Hagerman PJ 2003 the (CGG)n repeat element within the 5' untranslated region of the FMR1 message provides both positive and negative cis effects on in-vivo translation of a downstream reporter. Human Molecular Genetics 12, 3067-3074.

Fu YH, Kuhl DP, Pizzuti A et al. 1991 Variation of the CGG repeat at the fragile X site results in genetic instability: resolution of the Sherman paradox. Cell 67, 1047-1058.

Gleicher N, Weghofer A, Barad DH 2008a A pilot study of premature ovarian senescence: I. Correlation of triple CGG repeats on the FMR1 gene to ovarian reserve parameters FSH and anti-Müllerian hormone. Fertility and Sterility 91, 1700-1706.

Gleicher N, Weghofer A, Oktay K, Barad D 2008b The number of triple CGG repeats on the FMR1 gene: a new test reflective of diminished ovarian reserve and female infertility. Human Reproduction 23 (Suppl. 1), i204-5.

Gleicher N, Weghofer A, Barad DH 2008c A pilot study of premature ovarian senescence: II. Different genotype and phenotype for genetic and autoimmune etiologies. Fertility and Sterility 91, 1707-1711.

Hundscheid RDL, Braat DDM, Kiemeney LALM et al. 2001 Increased serum FSH in female fragile X premutation carriers with either regular menstrual cycles or on oral contraceptives. Human Reproduction 16, 457-462.

Murray A, Ennis S, MacSwiney F et al. 2000 Reproductive and menstrual history of females with fragile X expansions. European Journal of Human Genetics;8: 247-252.

Rohr J, Allen EG, Charen K et al. 2008 Anti-Mullerian hormone indicates early ovarian decline in fragile X mental retardation (FMR1) premutation carriers: a preliminary study. Human Reproduction 23, 1220-1225.

Singer T, Barad D, Weghofer A, Gleicher N 2008 Correlation of antimüllerian hormone and baseline follicle-stimulating hormone levels. Fertility and Sterility 91, 2616-2619.

Sullivan AK, Marcus M, Epstein MP et al. 2005 Association of FMR1 repeat size with ovarian dysfunction. Human Reproduction 20, 402-412.

Gleicher N, Weghofer A, Oktay K, Barad D. Can the FMR1 (fragile X) gene serve as predictor of response to ovarian stimulation? Reproduction Science (2008b) doi.10.1177/1933719108328617.

Wittenberger MD, Hagerman RJ, Sherman SL et al. 2007 The FMR1 premutation and reproduction. Fertility and Sterility (2007) 87,456-465.

Laggerbauer B, Ostareck D, Keidel E-M, Ostareck-Lederer A, Fischer U. Evidence that fragile X mental retardation protein is a negative regulator of translation. Human Molecular Genetics 2001; 10: 329-38.

Rife M, Nadal A, Milà M, Willemsen R. Immunohistochemical FMRP studies in a full mutated female fetus. American Journal of Medical Genetics 2004; 124A: 129-32.

Davidson A, Diamond B. Autoimmune diseases. N Engl J Med 2001; 345:340 50.

Tsigkou A, Marzotti S, Borges L, Brozzetti A, et al. High serum inhibin concentration discriminates autoimmune oophoritis from other forms of primary ovarian insufficiency. J Clin Endocrinol Metab 2000;93:1263-9.

Weghofer A, Barad D, Li J, Gleicher N. Aneuploidy rates in embryos from women with prematurely declining ovarian function: a pilot study. Fertility and Sterility 2007; 88: 90-4.

Munne S, Alikani M, Tomkin G, Grifo J, Cohen J. Embryo morphology, developmental rates, and maternal age are correlated with chromosome abnormalities. Fertility and Sterility 1995; 64: 382-91.

ACOG Committee Opinion. No. 338: screening for fragile X syndrome. Obstetrician and Gynecology. 2006; 107: 1483-5.

Sherman S, Pletcher BA, Driscoll DA. Fragile X syndrome: diagnostic and carrier testing. Genet Med 2005; 7: 584-7.

Burger NZ, Johnson JV Androgen production in women. In Androgens and Reproductive Aging. Tulandi T, Gelfand MM, eds; Tayloer and Francis, London and New York, 2006; pp. 1-4.

Weenen C, Laven JS, Von Bergh AR, Craufield M, Groome NP, Visser JA, Kramer P, fauser BC, Themmen AP. Anti-Müllerian hormone expression pattern in the human ovary: potential implications for initial and cyclic follicle recruitment. Molecular Human Reproduction. 2004; 10: 77-83.

Faddy MJ. Follicle dynamics during ovarian ageing. Molecular Cell Endocrinology 2000; 163: 43-8.

Fleming R. Recruitment prior to ovarian stimulation: ways of improving follicular recruitment. Reproduction Medicine Online 2005; 10: 55-9.

Altuntas CZ, Johnson JM, Tuohy VK. Autoimmune targeted disruption of the pituitary-ovarian axis causes premature ovarian failure. Journal of Immunology (2006) 177:1988-1996.

Bretherick KL, Metzger DL, Chanoine JP, Panagiotopoulos C, Watson SK, Lam WL, Fluker MR, Brown CJ, Robinson WP. Skewed X-chromosome inactivation is associated with primary but not secondary ovarian failure. American Journal of Medical Genetics (2007) 143A:945-951.

Bretherick KL, Hanna CW, Currie LM, Fluker MR, Hammond GL, Robinson WP. Estrogen receptor alpha gene polymorphisms are associated with idiopathic premature ovarian failure. Fertility and Sterility (2008) 89:318-324.

Bussani C, Papi L, Sestini R, Baldinotti F, et al. Premature ovarian failure and fragile X permutation: a study on 45 women. European Journal for Obstetrician and Gynecology Reproduction Biology (2004) 112:189-191.

Cameron M, Grover S, Moore P, Jayasinghe Y. Non-chromosomal, non-iatrogenic premature ovarian failure in adolescent population: a case series. Journal for Pediatric and Adolescent Gynecology (2008) 21:3-8.

Chand AL, Robertson DM, Shelling AN, Harrison CA. Mutational analysis of betaglycan/TGF-betaRill in premature ovarian failure. Fertility and Sterility (2007) 87:210-212.

Christin-Maitre S, Pasquire M, Donadille B, Bouchard P. Premature ovarian failure. Ann Endocrinol (Paris) (2006) 67:557-566.

Davis CJ, Davison RM, Payne NN, Rodeck CH, Conway GS. Female sex preponderance for idiopathic familial premature ovarian failure suggests an X chromosome defect: opinion. Human Reproduction (2000) 15:2418-2422.

Dixit H, Rao KL, Padmalatha VV, Kanakavalli M, Deenadayal M, Gupta N, Chakrabarty BN, Singh L. Mutational analysis of the betaglycan gene-coding region in susceptibility for ovarian failure. Human Reproduction (2006) 21:2041-2046.

(56) References Cited

OTHER PUBLICATIONS

Faddy MJ. Follicle dynamics during ovarian aging. Molecular Cell Endocrinology (2000) 163:43-48.

Faddy MJ, Gosden. A mathematical model of follicle dynamics in the human ovary. Human Reproduction (1995) 10:770-775.

Faddy MJ, Gosden RG. A model conforming the decline in follicle numbers to the age of menopause in women. Human Reproduction (1996) 11:1484-1486.

Gersak K, Meden-Vrtovec H, Peterlin B. Fragile X premutation in women with sporadic premature ovarian failure in Slovenia. Human Reproduction (2003) 18:1637-1640.

Geva E, Amit A, Lerner-Geva L, Lessing JB. Autoimmunity and reproduction. Fertility and Sterility (1997) 67:599-611.

Barad D, Gleicher N. Increased oocyte production after treatment with dehydroepiandrosterone. 2005; Fertil Steril 84:756.

Gleicher N, Weghofer A, Oktay K, Barad DH, "Correlation of triple repeats on the FMR1 (fragile X) gene to ovarian reserve: a new infertility test?" Acta Obstet Gynecol Scand 2009;88(9):1024-30.

Gleicher N, Weghofer A, Oktay K, Barad DH, "Relevance of triple CGG repeats in the FMR1 gene to ovarian reserve." Reprod Biomed Online, Sep 2009; 19(3): 385-90.

Gleicher N, Weghofer A, Barad DH, "Effects of race/ethnicity on triple CGG counts in the FMR1 gene in infertile women and egg donors." Reprod Biomed Online, Apr. 2010; 20(4): 485-491.

Gleicher N, Barad DH, "Can the FMR1 gene predict early ovarian aging?" Womens Health (Lond Engl), Mar. 2010; 6 (2): 165-9.

* cited by examiner

Table 1. Individual BRCA1/2 mutations in study group

| Mutation type n=64 | Frequency count |
|---|---|
| 1023delG | 1 |
| 1135insA | 1 |
| 1546dupCT | 1 |
| 185delAG | 1 |
| 1914del4 | 1 |
| 2041insA | 2 |
| 2798delGAAA | 1 |
| 3137delTTCA | 3 |
| 3427delA | 1 |
| 3473delGA | 1 |
| 3600del11 | 2 |
| 3773delT | 1 |
| 4088delA | 1 |
| 4143delT | 1 |
| 4233insA | 1 |
| 4512insT1428 | 1 |
| 4992del13 | 1 |
| 5343del5insG | 1 |
| 5382insC | 3 |
| 557ins25 | 1 |
| 5869delAAAT | 2 |
| 5873C>A (S1882X) | 2 |
| 5910C>G (Y1894X) | 1 |
| 6174delT | 1 |
| 6536C-A (S2103X) | 1 |
| 6580delGT | 1 |
| 6803del14 | 1 |
| 6869insC | 1 |
| 703+3A-G (IVS5+3A>G) | 1 |
| 7124insA | 1 |
| 795delT | 4 |
| 7994ins5 | 2 |
| 8034-2A-G (IVS16-2A>G) | 1 |
| 8074delT | 1 |
| 8230A-T (R2668X) | 1 |
| 8592G-A (W2788X) | 10 |
| 8715+1G>A (IVS19+1G>A) | 1 |
| 886del GT | 2 |
| 8983-1G>A (IVS21-1G>A) | 5 |
| 9325insA | 1 |
| 9610C>T(R3128X) | 1 |
| 962del4 | 1 |
| 9900insA | 1 |
| C61G | 2 |
| del20-24 | 1 |
| del5-14 | 1 |
| dup11B | 1 |
| dup2 | 1 |
| dup23 | 1 |
| E755X | 1 |
| IVS16 -2A>G | 1 |
| IVS16+3G>C | 1 |
| IVS20 -1G>C | 1 |
| IVS2-1G>C | 1 |
| K1727X | 1 |
| L1086X | 1 |
| L639X | 1 |
| Q1395X | 3 |
| Q1424X | 1 |
| Q563X | 5 |
| R1203X | 2 |
| R1751X | 2 |
| R71M | 1 |
| W321X | 1 |

METHOD OF TREATMENTS RELATED TO THE FMR1 GENE

CROSS REFERENCE TO RELATED APPLICATIONS

This application is a continuation-in-part of application Ser. No. 13/360,349, filed Jan. 27, 2012, which is a continuation-in-part of application Ser. No. 13/043,199, filed Mar. 8, 2011 and Ser. No. 12/508,295, filed on Jul. 23, 2009, which are all incorporated herein by reference in their entirety and for all purposes.

BACKGROUND

1. Field of the Invention

The subject matter presented herein relates to a method of determining risk of cancer and embryo health by evaluating CGG repeats on the FMR1 gene, and providing FMR1 related treatment.

2. Description of the Related Art

A dynamic triple-repeat sequence mutation in the X-linked gene, known as FMR1 (fragile X mental retardation 1), in its fully expanded form encompassing over 200 hypermethylated expansions of CGG, and expanding to the gene's promoter region, represents the full mutation for the so-called fragile X syndrome. Once the molecular biology of the syndrome was understood, it became apparent that between normal (or common) findings and full mutation, two additional stages of expansion exist, the so-called gray (or intermediate) zone and so-called premutations. There is consensus that premutations involve 55 to 200 repeats, and full mutations involve over 200 repeats. Whether the intermediate zone starts at 40 or 45 repeats has remained controversial, though, excluding American College of Obstetrics and Gynecology (ACOG) criteria, consensus is that the intermediate zone extends to 54 repeats.

Completely unaffected individuals most frequently demonstrate between 26 and 34 repeats with a median of approximately 30. Most laboratories, however, consider anything under 45 repeats a negative result. This may require reevaluation; because studies suggest that premature ovarian failure (POF) may be increased at intermediate-size alleles of approximately 41 to 58 repeats. Experts, recently summarizing the state of the art after two federally funded consensus meetings, concluded that more data was needed to confirm this latter association. The ACOG considers a patient unaffected with ≤40 repeats, intermediate with 41-60, and a premutation between 61 and 200 repeats.

Carriers of premutations do not suffer from classical symptoms of fragile X, such as mental retardation. Their alleles, however, are in subsequent generations at significant risk of further expansion to the fully developed mutation. Carriers are, nevertheless, phenotypically affected: males with premutations are at increased risk for the so-called fragile X-associated tremor/ataxia syndrome (FXTAS), a progressive neurodegenerative disorder, whereas affected women have only a very low risk for FXTAS, but experience a high prevalence of premature ovarian failure (POF).

True POF represents an end stage of ovarian function. In many instances it is reached quickly and without preceding symptoms and/or laboratory abnormalities. In other cases, it may be preceded by lengthy periods of clinically symptomatic diminished ovarian reserve. When young women demonstrate symptoms of diminished ovarian reserve, such as age-specific elevated baseline follicle stimulating hormone (FSH) levels and/or ovarian resistance to stimulation with gonadotropins, an acronym of premature ovarian aging (POA) has been coined to differentiate these clinical circumstances from end-stage POF patients and women with ovarian senescence because of advanced age.

Such differentiation is important because, in contrast to POF, POA patients still demonstrate a fair chance of pregnancy with autologous oocytes up to b-FSH levels of approximately 40 mIU/mL, and therefore, represent a milder degree of ovarian dysfunction than POF. POA patients share the underlying pathophysiologies and etiologies of POF [Gleicher et al. Do etiologies of premature ovarian aging (POA) mimic those of premature ovarian failure (POF)? Human Reproduction 2009; 24:2395-400]. Thus, it appears that at least some POA patients will transition into POF, and that therefore, at least in these patients, POA may represent a continuum of impaired ovarian function.

Furthermore, both the FMR1 gene (in its various mutations/genotypes and sub-genotypes) and the so-called BRCA1/2 gene mutations, a known contributor to the causes of breast and ovarian cancer, affect ovarian reserve. FMR1 genotypes and sub-genotypes also impact pregnancy chances in association with in vitro fertilization and define risk towards autoimmunity. Ovarian effects of BRCA gene mutations are, however, unclear. A better understanding of the interplay between BRCA1/2 mutations and the FMR1 gene, therefore, potentially may impact and improve screening for and therapeutic interventions in BRCA1/2-associated cancers. This may also result in improvement in determining a woman's pregnancy potential and accelerate appropriate clinical interventions and/or treatment for infertility related issues.

BRIEF SUMMARY OF THE INVENTION

BRCA1/2 mutations and recently described constitutional FMR1 genotypes have, independently, been associated with prematurely diminished ovarian reserve. Whether they interrelate in distribution, and whether observed effects of BRCA1/2 and FMR1 on ovaries are independent of each other, is unknown. In a prospective comparative cohort study (Example 1 below), we, therefore, investigated the distribution of constitutional FMR1 genotypes, normal (norm), heterozygous (het) and homozygous (hom), and of their respective sub-genotypes (high/low), in 99 BRCA1/2 mutation-positive women and 410 female controls to determine whether distribution patterns differed between study and control patients. In contrast to controls, BRCA1/2 carriers demonstrated almost complete absence of all constitutional FMR1 genotypes except for sub-genotypes with low ($CGG_{n<26}$) alleles (also referred to herein as FMR1(low)). Cross tabulation between BRCA1/2-positive patients and controls confirmed significant group membership, related to FMR1 distribution ($P<0.0001$).

These results offer as most likely explanation the conclusion that BRCA1/2 mutations are embryo-lethal, unless rescued by low ($CGG_{n<26}$) FMR1 sub-genotypes, present in approximately one quarter of all women. Women with low FMR1 sub-genotypes, therefore, should reflect increased BRCA1/2-associated cancer risks, while the remaining approximately 75 percent should face almost no such risks. If confirmed, this observation offers opportunities for more efficient and less costly BRCA1/2 cancer screening. The study also suggests that previously reported risk towards prematurely diminished ovarian reserve in association with BRCA mutations is FMR1-mediated, and offers a possible explanation for the so-called "BRCA paradox" by raising the possibility that the widely perceived BRCA1/2-associated tumor risk is actually FMR1-mediated.

More specifically, the fragile mental retardation 1 (FMR1) gene, located on the long arm of the X chromosome (Xq27.3) at base pairs 146,801,200 to 145,840,302, contains a repetitive DNA segment, the $CGG_n$ trinucleotide. The gene has, historically, primarily been investigated due to associated neuro-psychiatric risks at so-called premutation range CGG expansions (approximately $CGG_{n=55-200}$) and at full mutation range ($CGG_{n>200}$), the so-called fragile X syndrome (Willemsen et al, CGG repeat in the FMR1 gene: size matters. Clin Genet 80:214-25, 2011).

In women, the premutation range genotype of FMR1 has for decades been known associated with greatly increased risk towards premature ovarian failure (POF), often also called primary ovarian insufficiency (POI). The gene until recently was, however, not known for any specific associated ovarian phenotypes. This changed with the description of newly described constitutional, so-called ovarian genotypes of FMR1, with distinct phenotypical ovarian aging patterns, associated with prematurely diminished functional ovarian reserve and other associations.

These newly described ovarian genotypes of FMR1 were based on definition of a normal $CGG_n$ range of 26-34 (median $CGG_{n=30}$), later confirmed to be identical in all races, though in outliers (het and hom genotypes and sub-genotypes) demonstrating distinct distribution differences between races (Gleicher et al, Effects of race/ethnicity on triple CTT counts in the FMR1 gene in infertile women and egg donors, Reprod Biomed Online 20:485-491, 2010; and Gleicher et al, Association of FMR1 genotypes with in vitro fertilization (IVF) outcomes based on ethnicity/race PLoS ONE 6:e18781, 2011). The median of $CGG_{n=30}$ corresponded with the switching point between positive and negative message and peak translation of the gene product of FMR1 (Chen et al, The (CGG)n repeat element within the 5' untranslated region of the FMR1 message provides both positive and negative cis effects on in vivo translation of a downstream reporter, Hum Molec Genet 12:3067-74, 2003).

These new ovarian genotypes were also shown associated with IVF pregnancy chances, and to define risk towards autoimmunity in infertile patient populations (Gleicher et al, FMR1 genotype with autoimmunity-associated polycystic ovary-like phenotype and decreased pregnancy chance. PLoS ONE 5:e15303; Gleicher et al, Association of FMR1 genotypes with in vitro fertilization (IVF) outcomes based on ethnicity/race PLoS ONE 6:e18781, 2011).

Observing ovarian responses during in vitro fertilization (IVF), Oktay et al suspected in young BRCA mutation carriers with breast cancer a similar impairment in functional ovarian reserve as had been previously observed in association with certain FMR1 genotypes and sub-genotypes and, indeed, demonstrated such an association with BRCA1 (Oktay et al, Association of BRCA1 mutations with occult primary ovarian insufficiency: a possible explanation for the link between infertility and breast/ovarian cancer risks. J. Clin Oncol 28:240-4, 2010). Considering potential overlaps in BRCA1/2 and FMR1 genotypes and sub-genotypes, observed associations with BRCA1/2, however, do not necessarily have to be causal and, at least theoretically, could be related to overlapping FMR1 genotypes and sub-genotypes.

The commonality of prematurely diminished ovarian reserve, reported independently for BRCA mutations and the FMR1 gene, therefore, led us to investigate to what degree BRCA1/2 and FMR1 genotypes and sub-genotypes interrelate in distribution, and whether observed BRCA effects on ovarian reserve may be FMR1-mediated. As this study will demonstrate, the relationship between BRCA1/2 and the FMR1 gene was found to be surprisingly interdependent, raising a number of new biological questions of importance.

These findings lead herein to a disclosed method of screening a human for risk of malignancies. The method may include isolating the human's FMR1 gene, wherein the FMR1 gene has a first allele and a second allele, measuring the number of triple CGG repeats on each of the first and second alleles, wherein the measuring step is conducted through use of an assay, and identifying the human as at risk for cancer when the triple CGG repeat number for at least one of the first and second alleles is less than 26 (i.e., a low allele).

Further, a method of treating a human to reduce the risk or spread of malignancies is disclosed. The method includes administering an FMR1 inhibitor to the human to block expression of an FMR1 gene having at least one of two alleles with less than 26 triple CGG repeats (i.e., a low allele). This treatment may optionally include isolating an FMR1 gene from the human, measuring the number of triple CGG repeats on each allele of the isolated FMR1 gene by using an assay, and administering the FMR1 inhibitor to the human when a number of triple CGG repeats on at least one of the alleles of the isolated FMR1 gene is less than 26. Additionally, or alternatively, the method may include isolating the human's BRCA1 gene and BRCA2 gene, analyzing each of the BRCA1 and BRCA2 genes for mutations; and administering the FMR1 inhibitor when a BRCA1 or BRCA2 mutation exists. These methods of screening and treatment are not yet part of a standard of care for cancer and include new treatments never before used for these purposes.

Also a method of screening a human for increased embryo survival and embryo quality is disclosed. The method may include isolating at least one of the human's BRCA1 and BRCA2 genes, analyzing each of the BRCA1 and BRCA2 genes for mutations, isolating the human's FMR1 gene, wherein the FMR1 gene has a first allele and a second allele, when a mutation of at least one of the BRCA1 and BRCA2 gene is present, measuring the number of triple CGG repeats on each of the first and second alleles, wherein the measuring step is conducted through use of an assay, and identifying increased embryo quality and increased embryo survival, when the triple CGG repeat number for at least one of the first and second alleles is less than 26 (i.e., a low allele).

Further, a method of increasing embryo survival and embryo quality in an in vitro fertilization (IVF) laboratory is disclosed. This method includes locating at least one embryo of a female, and administering, to the embryo, an FMR1 enhancer to increase expression of an FMR1 gene with at least one allele with less than 26 triple CGG repeats to protect the female's embryos. In one form, the embryo receives the treatment in in vitro culture. In another form, the embryo is carrying a BRCA1/2 mutation or exhibiting slow growth in the IVF laboratory. This method may optionally include isolating the BRCA1 or BRCA2 gene from the embryo, determining whether the isolated BRCA1 or BRCA2 gene is mutated, and administering the FMR1 enhancer when the embryo has a mutated BRCA1 or BRCA2 gene. Since the presence of a BRCA1 or BRCA2 mutation in an embryo is embryo lethal in absence of a first or second FMR1 allele with less than 26 CGG repeats (i.e., a low allele), the FMR1 enhancer is added to embryos with BRCA1/2 mutation but in absence of such a low allele. In this case, the FMR1 enhancer may rescue such embryos, and potentially other slow growing embryos, from embryo lethality. These methods also are not part of any standard of care yet, and include a new composition in a new use such as administering FMR1 (low) to rescue embryos.

BRIEF DESCRIPTION OF THE DRAWINGS

FIG. 4 is a Table 1 listing detailed descriptions of BRCA 1/2 mutations in the study group;

DETAILED DESCRIPTION OF THE INVENTION

Figure 1:
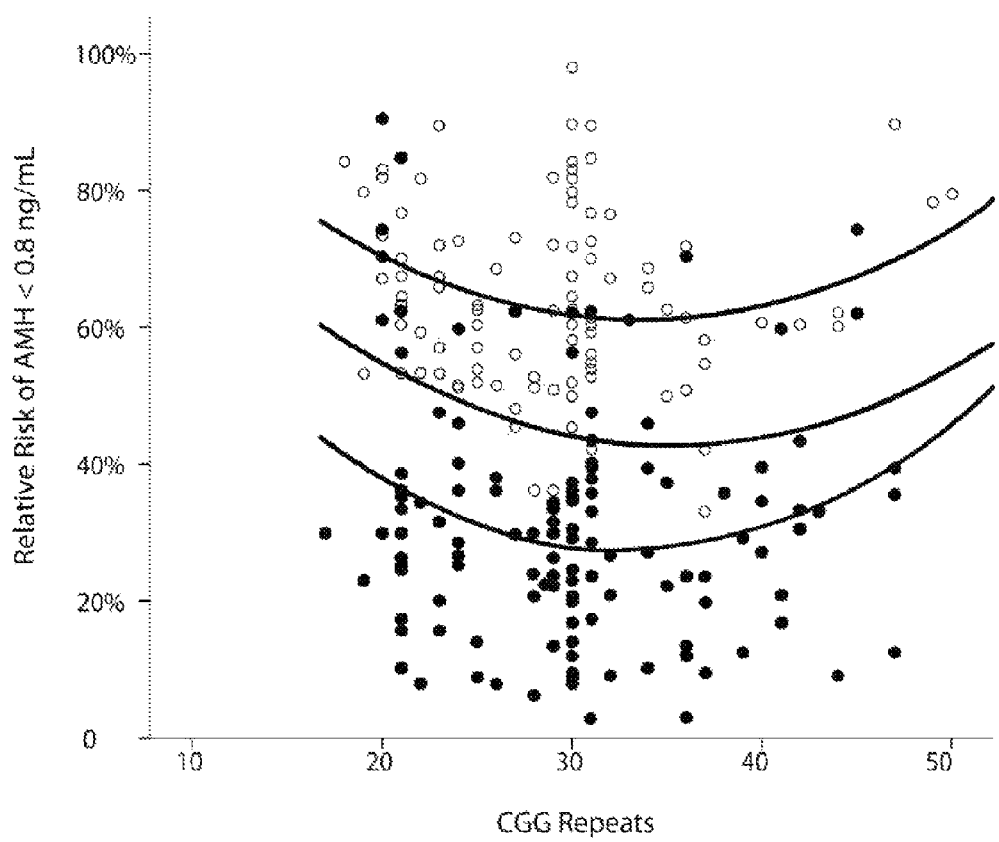
FIG. 1 is a logical regression of DOR (low AMH) and CGG counts, adjusted for age.

Herein, we use our new, previously totally unknown genotypes and sub-genotypes of the FMR1 gene, which have distinct diagnostic screening and/or testing functions. The genotypes and sub-genotypes are based on our recognition of a normal CGG triple repeat range of approximately 26-34, previously unknown. Up until we discovered this range, everything under 45 CGG repeats had been considered normal, 45 and above was considered abnormal, with 45-55 considered intermediate, 55-200 premutation, and over 200 full mutation. But even these "abnormals" have nothing to do with the diagnostic features characterized by the genotypes and sub-genotypes we describe herein.

Our genotypes and sub-genotypes statistically associate with specific clinical diagnoses/risks in 3 distinct medical areas: (i) infertility; (ii) autoimmunity; and (iii) cancer. The details of these areas are discussed more fully for (i) and (ii) in U.S. patent application Ser. Nos. 12/508,295, 13/043,199, and 13/360,349, which are all incorporated herein for all purposes. Other associations can be expected in the future. Therefore, these genotypes and sub-genotypes are new, based on the newly described normal range of (approximately) 26-34 triple CGG repeats.

Current medical knowledge neither allows for the prospective evaluation of ovarian function in young women, nor the accurate assessment of current ovarian function in infertile patients. A new test to predict ovarian function and assess female infertility is needed. The availability of a more objective measure of ovarian function would, therefore, improve the care of female infertility patients to a major degree.

As such, a new function for the FMR1 gene is defined herein (as opposed to the current function for the FMR1 gene that is only considered to affect neuropsychiatric issues). Specifically, the FMR1 gene affects ovarian function by regulating the amount of immature follicles released from ovarian storage, which a woman is born with, and, thereby, determining the "ovarian aging" process, which is a reflection of how many eggs still remain within the ovaries. The ability of the FMR1 gene allows us, based on CGG numbers, to predict whether someone is at risk for early ovarian aging.

Moreover, testing for triple-repeat sequence mutation in the FMR1 gene currently is carried out in four groups of patients. The first group includes boys showing characteristics of fragile X mental retardation. The second group includes middle-aged men showing symptoms of the so-called fragile X-associated tremor/ataxia syndrome (FX-TAS). The third group includes pregnant woman, to determine the risk of fragile X mental retardation in their unborn child. The fourth group includes a very small proportion of woman considering becoming pregnant, again to determine the risk of fragile X mental retardation in their yet-to-be conceived child.

Nowhere has the known standards of care in the healthcare industry included routine diagnostic tests using FMR1 to screen for ovarian aging and embryo health let alone cancer, and in turn the treatments herein involved with the control of FMR1 sub-genotypes. Thus, other groups of patients, including females with infertility issues or cancer patients for example, may benefit from analyzing the FMR1 gene with respect to ovarian function/reserve and/or cancer as disclosed herein.

Groups of Patients and Home Testing

Different set of patients may benefit from analyzing the FMR1 gene as disclosed herein. A first set includes women with a diagnosis of infertility. This set includes women who have been unsuccessful in conceiving after 6-12 months of attempting to become pregnant, for example. Testing for mutation in the FMR1 gene may be used to determine the etiology of the infertility. Infertility in most women results from a mutation in the FMR1 gene (genetic etiology) or results from autoimmunity (autoimmune etiology). Over ⅔ of all premature ovarian aging can be determined with evidence from the FMR1 gene and evidence of (even subclinical, i.e., only laboratory detectable) autoimmunity. Such testing may be coupled with a determination of autoimmunity, for example by looking for symptoms of other existing autoimmune disorders, such as psoriasis, lupus, etc, or actual testing for autoimmune antibodies.

A second set includes women who are not considering becoming pregnant, and who are deciding to delay having children. Women in this age set may be, for example 18-40 years old, more preferably 18-35 years old, including women at most 30 years old, especially 18-25 years old, including 18-23 and 18-22 years old. Also included may be women 25-40 years old, including 25-35 years old, and 25-30 years old. About 45% of the general female population will have a mutation in the FMR1 gene, here defined as one of her two alleles or both of her two alleles being outside of normal range (26-34 CGG repeats). Testing for this mutation, and the extent of the triple-repeat sequence mutation, will determine if a woman in this set is at risk for POA. Such testing may be coupled with a determination of autoimmunity, for example by looking for symptoms of other existing autoimmune disorders, such as psoriasis, lupus, etc, or actual testing for autoimmune antibodies. If a mutation is found, then action may be taken to monitor ovarian function, such as subsequent regular testing for AMH; this is particularly useful in those patient at least 25 years old (for example women 25-40 years old, including 25-35 years old, and 25-30 years old), as AMH levels will typically not indicate POA until the mid-twenties. Alternatively, or in addition, steps may be taken to address the risk of POA, for example by collecting and freezing eggs of the patient, a process called fertility preservation.

Many women in this second set may show no symptoms, and may not visit a doctor because they are not considering becoming pregnant; rather they are seeking to delay reproduction. Therefore, a kit for home collection of a DNA sample, together with preaddressed and optionally prepaid mailer, would allow such women to be tested for mutations in the FMR1 gene. Collection of a DNA sample may be done by sampling any one of a variety of tissues, with a tissue sampler, including skin from inside the mouth, such as a mouth swab, or a small blood sample, for example a lance prick of the finger or the arm, and the blood may be soaked into a small piece of absorbent paper, or a cotton swab. The kit may also include a questionnaire for determination of autoimmunity, for example by having questions regarding symptoms of autoimmune disorders. The DNA sample may be sent to a testing facility, such as a laboratory, to test the DNA sample for mutation in the FMR1 gene. The results of the test may then be provided directly to the patient, for example by results printed out and sent back to the patient, by electronic mail (e-mail), by telephone, or the patient may be directed to a website. Alternatively, results may be sent to a physician, such as a physician designated by the patient, or a physician designated by the supplier of the kit, either from a list, or a physician close to the patient selected via a website or by telephone, who can provide the test results to the patient.

Instruction may be included in the kit, in particular instructions for collection of the DNA sample, and optionally instruction regarding a questionnaire for determination of autoimmunity, or instruction regarding the results of the test, such as instructions for accessing the patient specific results through a website. The instructions may further include the intended use of the kit and/or test, and the instructions may state the ideal range of results. For example, the instructions may state that if a female's CGG repeats are within a normal or ideal range of 26-34 repeats with regard to ovarian function/reserve, then there is no indication of an increased risk for diminished ovarian aging or an increased risk or autoimmunity or an increased risk of cancer. Further, the instructions may explain the meaning of having CGG repeats within the normal range and/or action steps if the results are outside the ideal range. For example, if the CGG repeats are outside the normal range of 26-34 repeats, then the instructions may instruct the female to consult with a doctor for further evaluation, analysis and/or testing. For example, further testing may include tests for diminished ovarian reserve and/or for AMH levels, or may include BRCA1/BRCA2 analysis and testing.

A method of using a kit is disclosed. The kit may include a tissue sampler, a mailer preaddressed for a laboratory, and instructions comprising directing collection of tissue from a female considering delaying reproduction. The method may include collecting the tissue following the instructions, mailing the tissue to a laboratory for evaluation, receiving results from the laboratory, wherein the results include the number of CGG repeats on each allele of the female, and evaluating the results. Evaluating the results may include comparing the number of CGG repeats on each allele to a normal range of 26-34, and determining whether the number of CGG repeats are within the normal range, and if either number of CGG repeats is outside of the normal range, then the female is at an increased risk for early ovarian aging. Similarly, evaluating the results may include comparing the number of CGG repeats on each allele to a normal range of 26-34, and determining whether the number of CGG repeats are within the normal range, and if at least one of the numbers of CGG repeats is less than 26 (i.e., a low allele), then the female is at an increased risk for early ovarian aging, autoimmunity and/or cancer. For cancer or embryo health, a separate kit may be provided for screening for BRCA 1/2 mutations either before or after using a kit for screening of the FMR1 sub-genotype. Otherwise, a single kit may be provided for two separate DNA collections, one for each type of gene test, or the same, single tissue sample may be used for both tests.

Studies of FMR1 Gene

A summary of the studies using FMR1 is as follows and is described in detail in U.S. patent application Ser. Nos. 12/508,295, 13/043,199, and 13/360,349, also cited above. Relevant here, the studies determined that the FMR1 genotypes correlate to the ovarian reserve. For example, one study demonstrated a direct statistical association between number of triple CGG counts (at 35 to 55 repeats) and ovarian reserve, as reflected by anti-Müllerian hormone (AMH) levels. The higher the count, the higher the risk for premature ovarian senescence and severe ovarian compromise. Thus, the number of triple CGG repeats on the FMR1 gene is useful for diagnostic tests in the evaluation of female infertility. Further tests confirmed these results, thereby confirming the predictive value of FMR1 for risk of premature ovarian aging and infertility treatments such as the ovarian response to stimulation with gonadotropins and oocyte yield during in vitro fertilization (IVF).

Even further tests confirmed that the FMR1 gene influences the ovarian reserve, and that about 26 CGG repeats to about 34 CGG repeats represents a normal range with regard to ovarian function/reserve, as opposed to 40 CGG repeats to 45 CGG repeats representing normal with regard to neuropsychiatric risks. The gene appears to define life-long ovarian reserve patterns, with abnormal counts reducing ovarian reserve at younger, but improving it at advanced ages. The FMR1 gene, thus in some cases, may preserve fertility into older age at the expense of reducing fertility at younger ages.

With regard to specific sub-genotypes, we also concluded that utilization of new markers of ovarian reserve, such as AMH and CGG repeats one FMR1, will likely improve donor selection, thus reducing risks towards disappointing oocyte yields and hyperstimulation. It was found that normal and heterozygous (het) or homozygous (hom) abnormal counts on the FMR1 gene reflect distinct ovarian aging curves. Het abnormal can, however, be normal/low or normal/high, which may affect ovarian reserve (OR) differently. We then analyzed whether OR, reflected by anti-Müllerian hormone (AMH) and oocytes yield (phenotype), differs depending on FMR1 genotype, in 4 groups (norm, het-1, het-2, hom), stratified for age <35 and ≥35 years. We concluded that refinement in CGG count analysis of het abnormal women demonstrates distinct differences in ovarian aging patterns between het-1 and het-2 genotypes. Based on initially very high AMH in het-1 and observed habitués, the het-1 genotype appears to represent (normal weight) women with non-typical PCOS, who at young age unusually rapidly loose OR.

We also focused on the effects of CGG repeats when both alleles are in normal (norm) range or either 1 allele [heterozygous (het)] is abnormal or 2 alleles [homozygous (hom)] are abnormal. We concluded that ovarian aging differs based on norm, het or hom CGG counts, confirming an association between CGG repeats and ovarian reserve, and suggesting an FMR1 effect on follicular recruitment in favor of follicular preservation and fertility extensions into older age. Such functions potentially contribute to species maintenance, which may explain why the FMR1 gene is highly preserved despite obvious, and at often severe medical consequences primarily in males.

Remarks on the FMR1 Gene Studies

Although evidence from animal studies suggests that ovarian reserve is genetically controlled, it was undetermined how this genetic control works in humans. We have studied the effect of the FMR1 gene on ovarian reserve and for the first time demonstrated that the FMR1 gene plays a crucial role in ovarian aging. Probably most importantly, we defined new FMR1 genotypes and sub-genotypes, associated with specific ovarian aging patterns. In other words, based on a young girl's FMR1 gene pattern, one can predict how she, likely, will age her ovaries.

Almost all of our studies have been done in infertile women. While one can extrapolate, things may, nevertheless, be different in normally fertile women, especially while they are still young and unaffected by the physiological process of ovarian aging.

We, therefore, in one study, decided to investigate FMR1 genotypes and sub-genotypes in normal young egg donors, who had successfully donated. And low and behold, even at these very young ages there were already very significant differences in ovarian reserve between FMR1 genotypes and sub-genotypes.

These observations are of great potential clinical and scientific significance for a number of reasons: these findings will find their most practical and immediate application in egg donor selection. We now have another, highly accurate tool in selecting only the best possible donors for our patients.

The data also reemphasizes the importance of the FMR1 gene for female infertility. Women start their reproductive lives with different levels of ovarian reserve, and deplete their ovarian reserves at different speeds. How much ovarian reserve women start with and how quickly they depletes, of course, is the perfect definition of—"ovarian aging." The FMR1 gene, therefore, can be viewed as the ovarian aging gene.

One can foresee that this new knowledge about the genetic regulation of ovarian aging via the FMR1 gene will lead to better diagnostic tools and more successful therapeutic interventions in female infertility.

Additional Remarks on the FMR1 Gene as Regulator of Ovarian Recruitment and Ovarian Reserve Until now, nobody recognized that the premutation range of the CGG repeats may point toward a possible ovarian control function of the FMR1 gene.

Assessing a woman's CGG repeat numbers on the FMR1 gene may establish that a woman faces increased risk toward premature ovarian aging. Once this assessment is done, then a woman may be counseled and follow-up with regular ovarian reserve tests, such as anti-Müllerian hormone (AMH) levels. If such testing then reveals that a woman's ovarian reserve is prematurely diminishing, then she has adequate time to appropriately modify her reproductive planning and/or take steps to preserve fertility potential through assisted reproduction methods such as egg or embryo cryopreservation.

Ovarian function in all races/ethnicities appears defined by a normal range of 26 to 34 CGG repeats (mean 30), including the reported distribution peak of 29 to 30 repeats in humans and maximal gene translation, reported at 30 repeats.

Additionally, high CGG numbers (above 34) and low CGG numbers (below 29), both reflect risk toward POA/OPOI. FIG. 1 is a logistic regression of DOR (low AMH) and CGG counts, adjusted for age. The figure represents logistic regressions, demonstrating predictive relative risk of AMH <0.8 ng/mL over CGG counts, stratified for age—the upper curve is ≥38 years of age; the lower curve is <38 years of age; the middle curve is all ages. As shown in FIG. 1, every 5 CGG repeats below 30 increases the relative risk for low AMH by about 60%; Every 5 CGG repeats above 30 increases the relative risk for low AMH by about 40%. Open circles are women under age 38 and closed circles represent women above age 38 years. See FIG. 1.

Genotypes, defined by 2 normal count alleles (normal) demonstrate different OR aging patterns from women with 1 (heterozygous) or both alleles outside of range (homozygous). Heterozygous and homozygous genotypes recruit fewer follicles at younger ages, thus preserving OR into advanced age.

Figure 2:
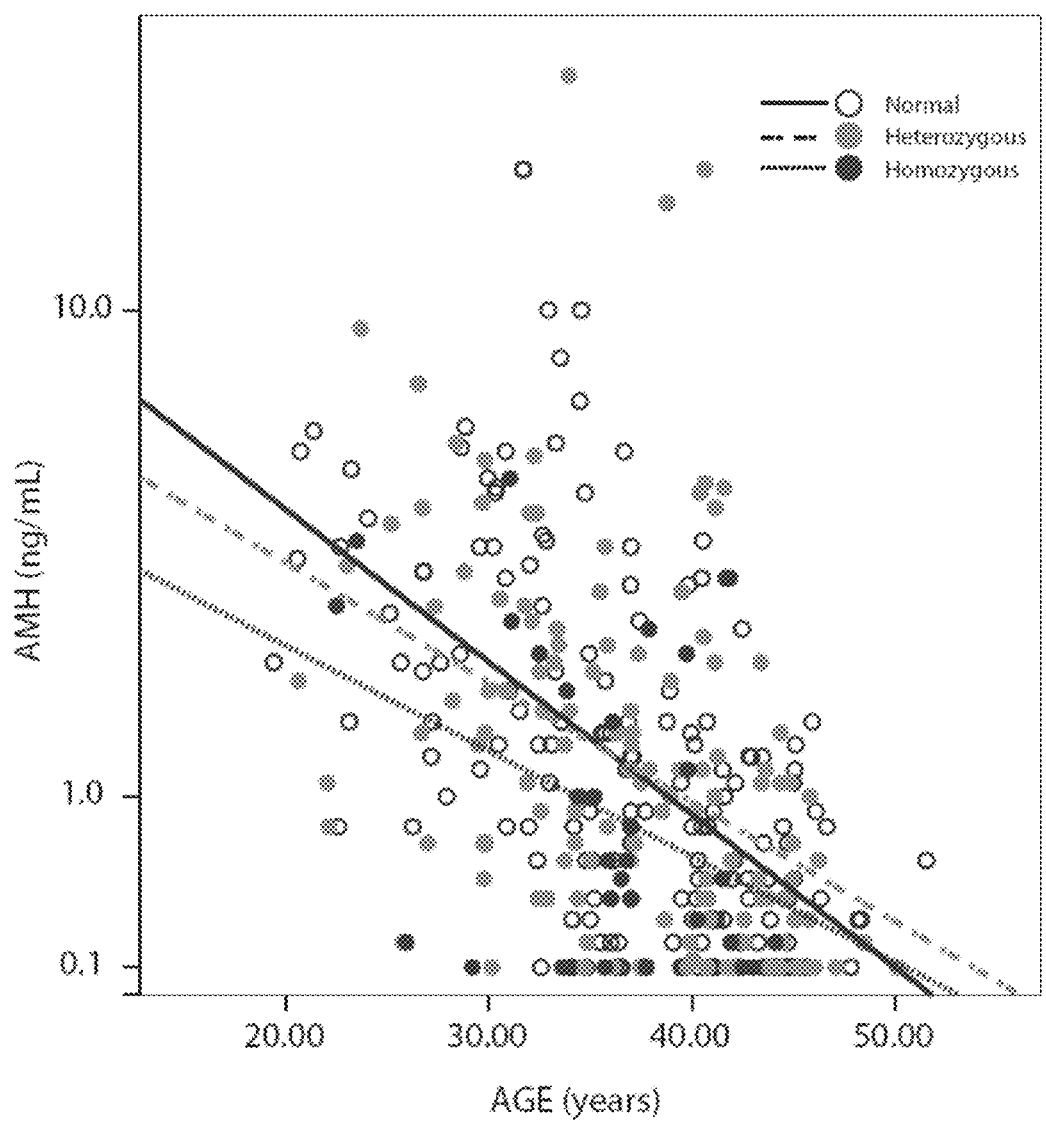
FIG. 2 is a linear regression of AMH levels, depending on genotypes normal (norm), heterozygous (het) and homozygous (hom).

In evaluating the OR controlling function of the FMR1 gene, at young ages: OR was the best in norm women, followed by het patients, with hom patients demonstrating the lowest reserve. OR patterns, however, changed with advancing age: women with norm genotype rapidly declined, while het and hom patients "aged" ovaries at a slower pace. Consequently, by about age 33 to about 34 years, AMH in women with norm genotype dropped below that of het genotypes and even below het genotypes in the late 40s. See at least FIG. 2. FIG. 2 shows a linear regression of AMH levels, depending on genotypes norm, het, and hom. The regression of norm patients crosses regression lines of het at approximately age 34 and of hom at approximately age 47 years.

Norm women deplete their OR much quicker than either het or hom patients. Thus, 2 alleles with normal CGG counts appear associated with active utilization of follicles/oocytes at young ages, and therefore, relatively rapid decline in remaining follicles, while het and hom genotypes demonstrate poorer recruitment at young ages and, therefore, comparably lower functional OR at such young ages, as assessed by AMH. Because of slower recruitment of primordial follicles at younger ages, these women, however, maintain a larger follicle pool into older age and, at more advanced ages, demonstrate better OR than norm women.

These observations suggest a direct FMR1 effect on follicular recruitment and OR and, therefore, on women's fecundity.

FMR1 Genotypes are Associated with Cancer Risks

Ovarian genotypes and sub-genotypes of the FMR1 gene in 99 BRCA1/2 mutation-positive Austrian breast cancer patients were investigated. There were significant differences in distribution as compared to 410 U.S. control females. BRCA1/2 carriers almost exclusively demonstrated only FMR1 genotypes and sub-genotypes with at least one low (CGG n<26) allele (referred to herein as FMR1(low)). This suggests embryo-lethal effects of BRCA1/2 in humans, unless embryos are rescued by low FMR1 genotypes or sub-genotypes. Cross tabulation between the comparison group and BRCA1/2-positive cancer patients confirmed significant group membership, related to FMR1 distribution (P<0.0001). If low genotypes/sub-genotypes of FMR1 rescue human embryos from BRCA1/2-associated lethality, they have to reflect increased cancer risks associated with BRCA1/2 mutations. Occurring in approximately 25 percent of women, low FMR1 genotypes and sub-genotypes, therefore, expand risk for BRCA1/2-associated cancers to approximately one quarter of the female population, while reducing risk in the remaining three-quarters, potentially revolutionizing cancer screening for breast, ovarian and other malignancies in women. In short, BRCA1/2 are embryo lethal human gene mutations, which are rescued by low count (CGG n<26) FMR1 (also referred to herein as FMR1 (low)) mutations. As such, women with CGG n<26 may suggest a new target of females that may be screened for female cancer, such as breast and/or ovarian cancer. This also suggests that treatment with an FMR1 (low) inhibitor may reduce the risk or spread of such cancer, while treatment enhancing FMR1 (low) expression may increase embryo survival or embryo quality when a BRCA 1/2 mutation is present. See at least Example 1 below.

Various Aspects of the Method and Apparatus

A method of screening a human for risk of malignancies such as malignant tumors or cancer for example is disclosed. The method may include isolating the human's FMR1 gene, wherein the FMR1 gene has a first allele and a second allele, measuring the number of triple CGG repeats on each of the first and second alleles, wherein the measuring step is conducted through use of an assay, and identifying the human as at risk for cancer when the triple CGG repeat number for at least one of the first and second alleles is less than 26 (i.e., low allele). The method also may include identifying the human as at risk when the triple CGG repeat number for at least one of the first and second alleles is between 26-34. The method may include identifying the human as at risk when the triple CGG repeat number for each of the first and second alleles is less than 26 (low allele). The method further may include identifying the human as at risk when the triple CGG repeat number for at least one of the first and second alleles is greater than 34 (high allele). Also, the method may include identifying the human as at risk for at least one of breast cancer and ovarian cancer. The human may be female. The assay may be at least one of Southern blotting and polymerase chain reaction. Additionally, the method may include conducting a secondary test by isolating the human's BRCA1 gene and the BRCA2 gene, analyzing each of the BRCA1 and BRCA2 genes for mutations by performing at least one of denaturation high performance liquid chromatography and chain-terminating inhibitors. Also, the method may include confirming the presence of cancer by conducting a secondary test and analyzing the results of the secondary test.

A method may include administering to the human at least one of a gene blocker or a therapeutic drug to interfere with the cancer. Such a method of treating a human to limit the risk or spread of malignancies may include administering an FMR1 inhibitor to the human to block expression of an FMR1 gene having at least one of two alleles with less than 26 triple CGG repeats (i.e., low allele). This treatment may be performed after screening for mutated BRCA1 or BRCA2 genes and/or screening for FMR1 (low) sub-genotype.

Furthermore, a method of screening a human for increased embryo quality is disclosed. The method may include isolating at least one of the human's BRCA1 and BRCA2 genes, analyzing each of the BRCA1 and BRCA2 genes for mutations, isolating the human's FMR1 gene, wherein the FMR1 gene has a first allele and a second allele, when a mutation of at least one of the BRCA1 and BRCA2 gene is present, measuring the number of triple CGG repeats on the FMR1 gene each of the first and second alleles, wherein the measuring step is conducted through use of an assay, and identifying increased embryo quality and increased embryo survival, when the triple CGG repeat number for at least one of the first and second alleles is less than 26 (low).

A method of treatment for increasing embryo survival or embryo quality is disclosed, and includes administering to an embryo, an FMR1 enhancer to increase expression of an FMR1 gene with at least one allele with less than 26 triple CGG repeats or mimic such an expression in absence of a low FMR1 allele. This may occur after determining the embryo has a mutated BRCA1 or BRCA2 gene. This treatment may be provided even though the embryo already has the FMR1 (low) sub-genotype in order to further increase the FMR1 (low) gene expression or such treatment may also be effective in other states of slow embryonic growth.

Also, the methods above may include reporting results of the testing to the female. The reporting may include sending the results of the testing to the female. The reporting further may include making the results available to the female on a website. Further, the method may include providing to the female a kit for collecting the DNA sample. The kit may include a container for holding the DNA sample, and a mailer for sending the DNA sample to a testing laboratory.

Moreover, a kit for determining the FMR1 genotype or sub-genotype and/or BRCA 1/2 mutation is disclosed. The kit may include a tissue sampler, a mailer preaddressed for a laboratory, and instructions including directing collection of tissue from a female considering delaying reproduction. The kit also may include a questionnaire containing questions regarding symptoms of cancer and/or infertility. The tissue sampler may be a swab for collecting tissue from within the female's mouth. Further, the tissue sampler may be a blood sampler. The instructions may include instruction for collecting test results from a website.

Additionally, a method of using a kit is disclosed. The kit may include a tissue sampler, a mailer preaddressed for a laboratory, and instructions comprising directing collection of tissue from a female. The method may include collecting the tissue following the instructions, mailing the tissue to a laboratory for evaluation, receiving results from the laboratory, wherein the results include the number of CGG repeats on each allele of the female, and evaluating the results. Evaluating the results may include comparing the number of CGG repeats on each allele to a normal range, and determining whether the number of CGG repeats are within the normal range, and if either number of CGG repeats is outside of the normal range, then the female is at an increased risk for early ovarian aging, autoimmunity, and/or cancer.

Treatments for Cancer by Controlling FMR1 Expression

As explained above, the FMR1(low) sub-genotype deinhibits the antiproliferative effect of BRCA1/2 mutations in embryonic tissue, rescuing embryos from embryo lethality, while similarly deinhibiting the anti-proliferative effect of BRCA1/2 mutations in BRCA1/2-associated cancers, here causing a negative effect; i.e., cancer proliferation and growth. (These apparently opposing effects of BRCA1/2 on embryonic and cancer tissues have been called the "BRCA paradox," which has remained unexplained until the deinhibitory effect of a low FMR1 allele (<26 triple CGG repeats) on BRCA1/2 was recognized). Thus, it is believed that tumor growth may be slowed, stopped, or even prevented by inhibiting the expression of the FMR1 (low) sub-genotype when present.

To inhibit transcription or translation of the FMR1 gene, one approach is to inhibit protein expression using an FMR1 inhibitor including small interfering RNAs (siRNA) which may block translation or transcription. The FMR1 protein is thought to be involved in the RNA interference machinery so that upon initial binding of siRNAs to their target sequence, the machinery may become compromised and unresponsive to further inhibition. This may result in minimal inhibition. Nevertheless, it is believed that an inhibitor with siRNA will be helpful because it is known that even partial inhibition of FMR1 expression with antisense RNA may have significant physiological effects.

A molecular delivery platform that specifically targets siRNA to breast tissues has been described in a mouse model of breast cancer (Lieberman and Song at http://stm.sciencemag.org/content/4/130/130ra48.abstract?sid=b77004fe-f0a9-427a-b724-3c557a1acf96). The platform consists of a combination of an antibody fragment, which binds to a protein expressed only on the surface of breast cancer tissue, and a packaging peptide that stabilizes and delivers the RNA molecule to tumors, resulting in silencing of the gene of interest and preventing tumor growth and metastasis. The advantage of such a system is that it avoids systemic silencing of FMR1 in tissues where its function is essential (which may lead to toxicity and/or inflammation), as well as avoiding the opposite undesirable effect of clearance of the siRNA before it had the chance to exert its effect.

The efficiency of FMR1 downregulation in response to siRNA (compared with nontransfected cells) may be assayed by semiquantitative reverse transcription polymerase chain reaction (RT-PCR) and protein depletion can be assessed by immunoblotting.

Finally, pharmaceutical FMR1 inhibitors may be used that specifically inhibit the activity of FMRP (Fragile X Mental Retardation Protein) toward its cellular ligand. Forming such biochemical inhibitors require knowledge of the three-dimensional structure of FMR1, which is available from X-Ray Crystallography and NMR (Nuclear Magnetic Resonance) data.

Another approach for enhancing (or weakening) the effects of FMR1 alleles involves manipulating the transcription factors that regulate its expression. The length of the CGG-repeat tract (or in other words the number of triple CGG repeats) in the 5'-untranslated region of the FMR1 gene plays a dominant role in dictating the affinity of various transcription factors to upstream DNA elements, as well as the cooperative behavior between them. For instance, the transactivation capacity and synergism between these transcription factors is influenced by the methylation and heterochromatin state of the DNA upstream of the coding sequence of FMR1, which is in turn affected by the length of the CGG repeat. Three of the transcription factors that regulate the expression of FMR1 associate with BRCA1: (1) ZF5 which is a repressor of transcription that binds the CGG repeats directly (Gorski et al., 2011), (2) USF2 which binds the promoter region and is downregulated in breast cancer cell lines (Ismail et al., 1999), and (3) AP2-α which is an activator of transcription and that selectively regulates FMR1 during embryonic development (Lim et al., 2005).

For instance, human transcription factor ZF5 is a known repressor of FMR1, and the repression is mediated by direct interaction with CGG repeats of the gene. Downregulation of ZF5 by RNA interference causes upregulation of the FMR1 gene, whereas overexpression of ZF5 represses transcription (Orlov et al., 2007). Overexpression is performed by gene therapy introducing ZF5 on a vector. CGGBP1 (CGG triplet repeat binding protein 1) has similar effects on FMR1 expression (Muller-Hartmann et al., 2000). Thus, inhibiting these repressor proteins by RNAi or with a drug that prevents its binding to DNA, or alternatively, enhancing it with gene therapy will have an effect on FMR1 expression. For an activator like AP2-α, the opposite would be used. RNAi would be used to downregulate AP2-α to downregulate or block the FMR1 gene, while overexpression of AP2-α by gene therapy, for example, causes enhancement or upregulation of the FMR1 gene. Similarly, inhibiting or enhancing the expression of the transcription factors discussed above, as well as NRF1, SP1, SP3, USF1 were shown to regulate the expression from the FMR1 promoter (Smith et al., 2004; Kumari et al., 2005; Kumari and Usdin, 2001; Smith et al., 2006), can also be used as a means to up- or down-regulate the expression of FMR1.

Regarding the procedures for the diagnosis and treatment, genetic cancer screening for BRCA1/2 mutations is currently restricted to high risk families for breast and ovarian cancer. A large pool of females, considered at lower risk for such cancers or at risk for other types of BRCA mutation related cancers are, therefore, currently not screened for the BRCA1/2 mutations due to the high cost for the BRCA screening. In light of the herein discovered relationship between BRCA mutations and FMR1 (low), and the fact that FMR1 screening, in contrast to BRCA screening, is substantially lower in cost, the screening for the FMR1 (low) sub-genotype can be used as a routine initial screening for the BRCA1/2 mutation, thereby providing a great benefit to society. By one approach, only when a person is found to have the FMR1 (low) sub-genotype will that person undergo BRCA1/2 mutation screening as a secondary test.

The FMR1 blocking treatment, however, may not always need to be provided after a secondary test. Thus, depending on the circumstances, a patient may receive the FMR1 blocking treatment whether or not she has been screened for BRCA1/2 mutations. Also, a person may be treated with the FMR1 blocker without first receiving the FMR1 (low) sub-genotype screening as well. For example, a person with BRCA1/2 mutations may receive the FMR1 blocking treatment prophylactically as a precaution to limit risk of cancer when the BRCA1/2 mutation is present. It should be noted that typically the person or patient may be female or male, and that while breast and ovarian cancers are usually targeted other cancers may be targeted as well.

Treatments to Increase Embryo Quality or Survival by Increasing FMR1 Expression

As mentioned above, BRCA1/2 mutations appear to be embryo lethal unless FMR1 low-subgenotype is present to reinstate cellular proliferation and rescue the embryo. To achieve this scenario, namely, to increase the expression from the FMR1 allele bearing the short (less than 26) CGG repeat, somatic gene therapy can be employed to introduce the short FMR1 allele on a vector, as has been used for diseases caused by single-gene defects. Using a tissue-specific promoter, it is also possible to target the gene to the breast or other desired tissue. Again, pharmaceutical agents may be used to specifically enhance the activity of FMRP toward its cellular ligand. Forming such biochemical enhancers require knowledge of the three-dimensional structure of FMR1, which is available from X-Ray Crystallography and NMR (Nuclear Magnetic Resonance) data.

Otherwise, the transcription factors may be used to enhance the FMR1 (low) expression as described above.

With regard to the treatments, in one form, gene therapy or the other methods described herein may be provided to enhance FMR1 (low) expression after it is determined that the embryo carries BRCA1 or BRCA2 mutations by the screening methods described herein, and therefore needs embryo rescuing by the FMR1(low) sub-genotype if such subgenotype is not naturally present in the embryo. Thus, in one form, the FMR1 enhancer is provided after screening for BRCA1 or BRCA2 mutations. In another form, screening for FMR1 (low) occurs first, and if present, then screening for BRCA1 or BRCA2 mutations is performed. It will be appreciated, however, that the risk of the presence of the BRCA1 or BRCA2 mutations might be assumed by screening for, and presence of, the FMR1 (low) sub-genotype alone. Regardless, in one form, if the FMR1 (low) sub-genotype is naturally present, the treatment is omitted. In other forms, the treatment may be provided even though FMR1 (low) natural already is present, to further enhance expression, or when slow embryonic growth exists.

Example 1

Objective of Example 1

FMR1 as well as BRCA genes may affect ovarian reserve. Based on a normal range of 26-34 (median 30) CGG repeats, different ovarian FMR1 genotypes and sub-genotypes have been described and have been associated with varying ovarian aging patterns. While the normal range of CGG repeats is constant, prevalence of genotypes and sub-genotypes varies between races. They also affect pregnancy chances in association with in vitro fertilization (IVF), and define risk towards autoimmunity in infertile women.

Ovarian effects of BRCA genes are less well defined: BRCA1 but not BRCA2 has been associated with occult primary ovarian insufficiency. This commonality between BRCA and FMR1 led us to investigate associations between FMR1 and BRCA1/2.

Method and Materials of Example 1

Study Groups

The study involved two distinct patient populations: (i) 99 female BRCA1 or BRCA2 mutation positive breast cancer patients. Their BRCA1/2 testing was performed at the Medical University Vienna, Vienna, Austria, while their FMR1 assays were performed at the Medical University Graz, Graz, Austria. (ii) 410 female infertility patients, whose anonymized clinical information, including FMR1 testing results, were stored in the electronic research data base of the Center for Human Reproduction in New York, U.S.A.

Coordination of research efforts between Austrian and U.S. centers was involved, such that the BRCA1/2 and FMR1 data of the Austrian breast cancer patients could be statistically analyzed, anonymized and in bulk.

When an initial statistical analysis determined the presented data here, questions arose about compatibility of Austrian and U.S. FMR1 results. The Austrian laboratory was, therefore, requested to provide random anonymized results of a patient population reflecting the whole CGG spectrum. FMR1 genotypes and sub-genotypes of 105 such patients did not differ significantly in either median or distribution between $25^{th}$ centile and $75^{th}$ centile from infertile U.S. controls.

Laboratory Analyses

As noted, BRCA1/2 and FMR1 analyses of the Austrian study group were performed in Vienna (BRCA1/2) and Graz (FMR1), respectively. Until and inclusive of 2008, BRCA1/2 analyses were performed by denaturation high performance liquid chromatography, as previously reported by the laboratory. After 2008 DNA sequencing, with use of chain-terminating inhibitors was utilized.

FMR1 analyses in Austria were performed as previously in principle reported from the New York laboratory. In brief, DNA-concentration and purity were determined by measurements with a NanoDrop ND-1000 Spectrophotometer. A Fragile X PCR Screen Kit (Abbot Molecular, Vienna, Austria) was utilized to detect expanded $CGG_n$ in the 5' untranslated region of FMR1. PCR was set up in total volume of 20 μl (13 μl High GC PCR Buffer; 0.8 μl FMR1 Primers-2; 1.2 μl TR PCR Enzyme Mix; 2 μl DNase/RNase free water; and 3 μl genomic DNA at concentration of 10 mg/μl) and performed with a PTC200 Thermocycler (Biorad, Vienna, Austria; Cycling conditions: 98.5° C. for 30 seconds; 53° C. for 30 seconds and 75° C. for 1 minute with 50 cycles). PCR products were stored at −20°.

Capillary electrophoresis was performed by mixing 2 μl of PCR product with 20 μl Hi-Di™ formamide (Applied Biosystems, Foster City, Calif., USA) and 2 μl of ROX™ 1000 Size Standard (supplied with above noted Fragile X Kit), and incubating at 95° for 2 minutes to denature the DNA, followed by immediate cooling to 25°. Samples were then loaded into an ABI 3100 Sequencer (Applied Biosystems), using a 36 cm array and POPE polymer. Injection and run conditions were set according to protocol, provided with above noted Fragile X Kit. GeneMapper software v3.5 (Applied Biosystems) and electropherograms were used to determine $CGG_n$.

New York FMR1 analyses were performed by commercial assays, as previously reported. In brief, DNA analysis was performed by PR amplification, followed by agrose gel, as well as capillary electrophoresis and Southern blot analysis, using the probe StB12.3 and restriction enzymes EcoR1 and Eag1.

Austrian FMR1 data were reported for both alleles as CGG and in New York converted to the format of ovarian genotypes and sub-genotypes. In brief, it is based on a normal range of $CGG_{n=26-34}$, with median of 30 repeats. Women, therefore, can have the following genotypes: normal (norm) if both alleles are in normal range; heterozygous (het), if one allele is in and one outside of normal range; and homozygous (hom) if both alleles are outside normal range. Het and hom genotypes can then be further subdivided, depending whether abnormal alleles are above (high) or below (low) normal range into het-norm/high and het-norm/low and hom-high/high, hom-high/low and hom-low/low sub-genotypes. Because of the small number of hom patients, they are not sub-divided into sub-genotypes in this study.

Statistical Analysis

Proportions of FMR1 genotypes and sub-genotypes were compared between the two study groups using cross-tabulations and calculations of Chi-square and Cramer's V statistics. When comparing $CGG_n$ as a continuous function between the groups, nonparametric testing was used because $CGG_n$ in populations tends to be positively skewed. Mann-Whitney U tests were conducted to evaluate differences between the two groups on median change in $CGG_n$ of both alleles.

All statistical calculations were performed utilizing SPSS, version 18 (Chicago, Ill.).

Results and Discussion of Example 1

The study involved two distinct patient populations: (i) 99 Austrian, BRCA1/2-positive breast cancer patients; (ii) 410 U.S. based infertility patients, who underwent FMR1 testing and served as comparison population [a similar infertility population previously was shown to demonstrate similar CGG count distributions to a general population].

Austrian and U.S. Institutional Review Boards (IRBs) approved investigation of respective patient populations.

Figure 3:
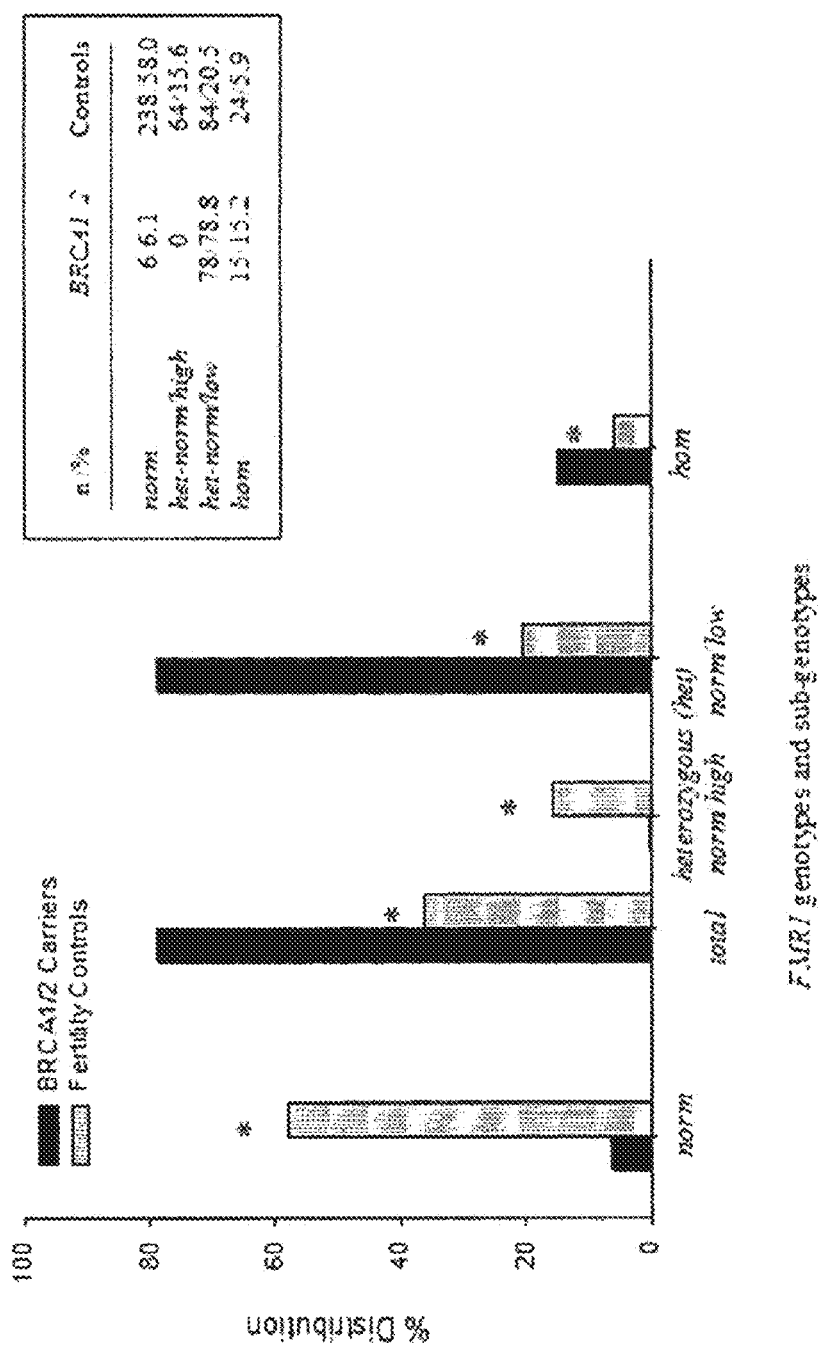
FIG. 3 is a graph showing the distribution of FMR1 genotypes and sub-genotypes in women with BRCA1/2 mutations and U.S. comparison group.

FIG. 3 shows the distribution of FMR1 genotypes and sub-genotypes in women with BRCA1/2 mutations (black bars) and U.S. (gray) comparison group are shown in FIG. 3; the "*" within each category denotes significance at P<0.05. FIG. 4 (Table 1) provides a detailed description of BRCA 1/2 mutations in the study group. Noteworthy are the excess of het-norm/low and complete absence of het-norm/high in FMR1 sub-genotypes in BRCA1/2 mutation carriers, and the very low prevalence of women with norm FMR1 genotype. A numerical presentation of these data is presented in FIGS. 5-6 and 7-8. In these figures, genotypes "norm" stands for normal, "het" is for heterozygous and "hom" is for homozygous, and further, in description of sub-genotypes, high stands for CGG n>34, and low for CGG n<26.

Infertile control patients demonstrated similar FMR1 genotypes and sub-genotype distribution as reported before in such populations (FIG. 3), with normal (norm), heterozygous (het) and homozygous (hom) genotypes of 58.0, 36.1 and 5.9 percent, respectively. The expected distribution was also observed with sub-genotypes, with het-norm/high at 15.6 percent and het-norm/low at 20.5 percent. This distribution of $CGG_n$ also follows that in general populations.

Table 1 (FIG. 4) provides a detailed description of BRCA 1/2 mutations in the study group.

In contrast, as FIG. 3 also demonstrates, BRCA1/2-positive women presented with substantially or distinctively different FMR1 genotype and sub-genotype distributions: A large majority of BRCA1/2 women were found to exhibit the het-norm/low FMR1 sub-genotype (74.0% BRCA1 and 83.7% BRCA2, respectively). Combined, 78.8 percent of women who were BRCA1 or BRCA2 positive exhibited the het-norm/low FMR1 sub-genotype. Moreover, in stark contrast to controls, no BRCA1/2 carriers, at all, demonstrated the het-norm/high FMR1 sub-genotype.

Similarly, BRCA1/2-positive patients demonstrated almost no norm genotypes, otherwise the most frequently represented single genotype in the comparison population (FIG. 3): Only 10.0 and 2.0 percent of BRCA1 and BRCA2 patients, respectively (combined 6.1%), demonstrated a norm FMR1 genotype.

The hom genotype was mildly overrepresented in BRCA1 and BRCA2 carriers (16.0% and 14.3%, respectively; combined, 15.2%). Numbers were too small for meaningful assessments of sub-genotypes.

In comparing distribution of FMR1 genotypes and sub-genotypes between BRCA1/2 patients and U.S. controls (with hom patients collapsed into one group), group membership was significantly related [$x^2$ (6, N=614)=158.71; P<0.0001).

As shown by cross tabulations, there were significant relationships between group membership and FMR1 genotypes/sub-genotypes. Non-parametric testing (Mann-Whitney U test)) confirmed statistically significant differences in median change for $CGG_n$ on the low count allele of the FMR1 gene between both patient groups, with follow up tests (Dunn's Method) indicating significant differences between groups (See FIGS. 5, 6, 7 and 8 showing the distributions of individual $CGG_n$ in all three patient populations).

Figures 5, 6:
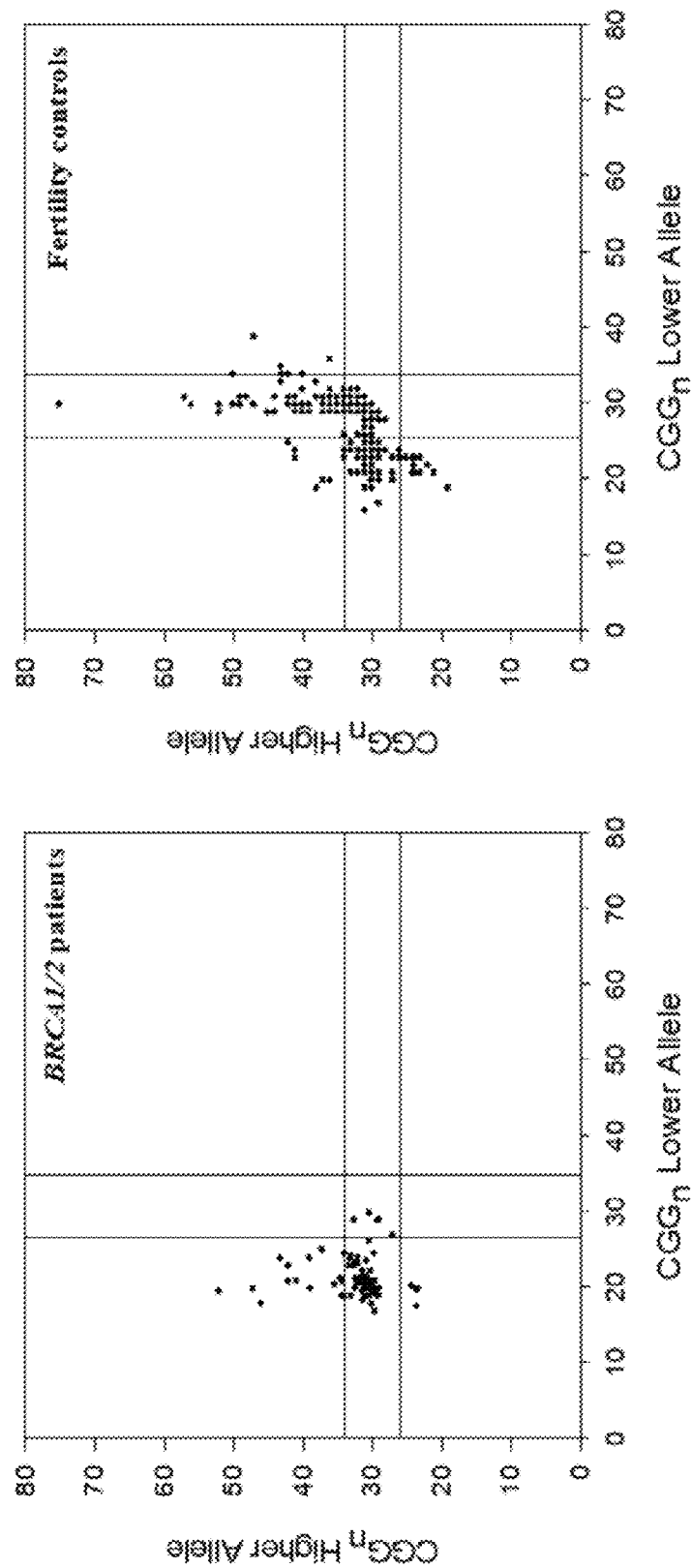
FIG. 5 is a graph showing the distribution of FMR1 alleles in BRCA1/2 carriers, and the horizontal and vertical parallel lines define the normal distribution area.
FIG. 6 is a graph showing the distribution of FMR1 alleles in the fertility controls, and the horizontal and vertical parallel lines define the normal distribution area.
Figures 7, 8:
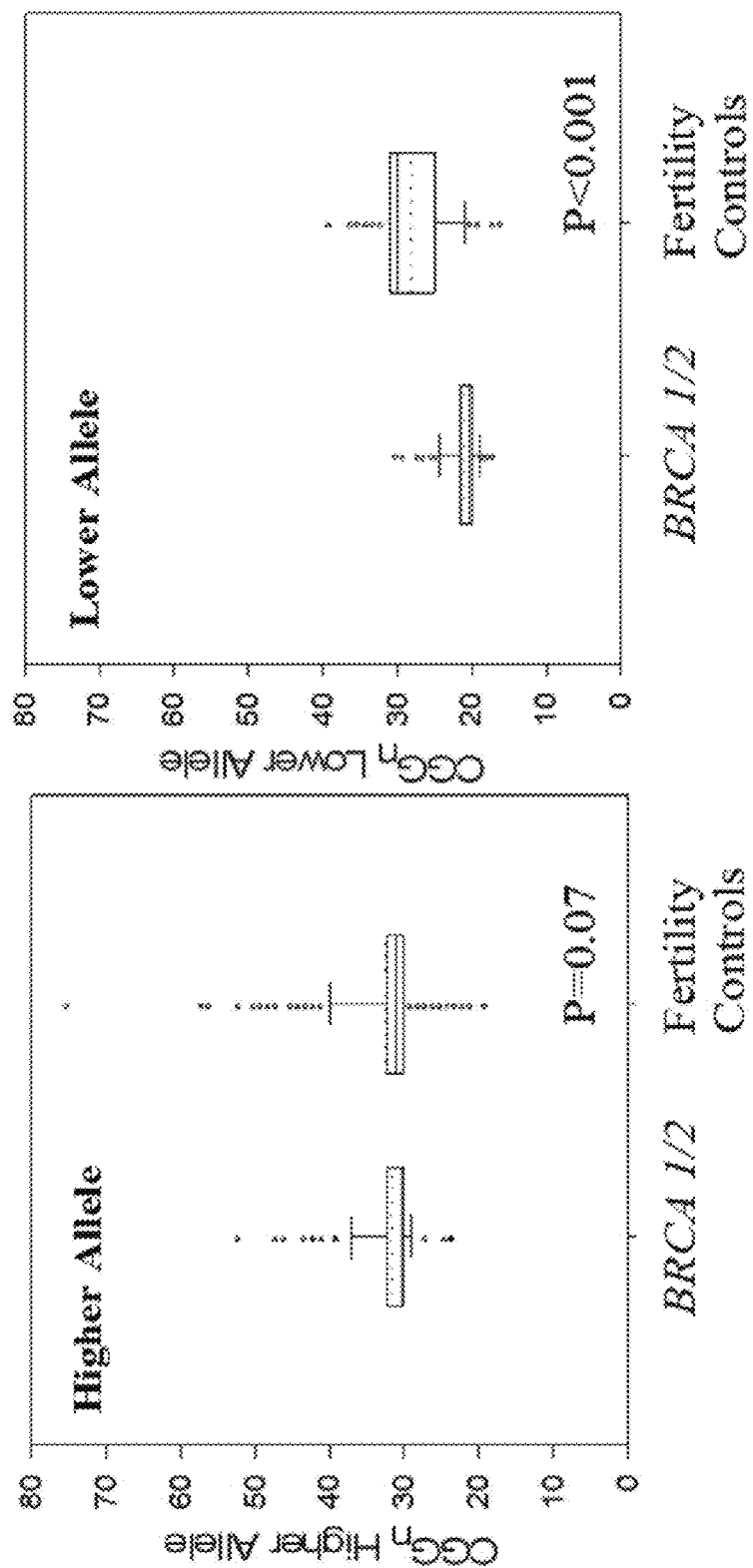
FIG. 7 is a graph showing the distribution of FMR1 genotypes and sub-genotypes in women with BRCA1/2 mutations and U.S. comparison group.
FIG. 8 is a graph showing the distribution of FMR1 genotypes and sub-genotypes in women with BRCA1/2 mutations and U.S. comparison group.

FIGS. 5 and 6 show the distribution on both FMR1 alleles, of CGG in BRCA1/2 mutation carriers as well as U.S. controls in the form of scattergrams. Horizontal and vertical parallel lines in scattergrams define the norm distribution area ($CGG_{n=26-34}$), with areas below and above representing low and high, sub-genotypes, respectively; FIGS. 7 and 8 represent higher and lower count allele, respectively, for individual patients. Only the lower count allele varied significantly between the two groups (Mann-Whitney U test, P<0.001). FIGS. 18b and 18b scattergrams, as well as FIGS. 19a and 19b, demonstrate graphically the significant shift towards low FMR1 sub-genotypes, especially on the lower count allele of BRCA1/2 mutation carriers. In FIGS. 19a and 19b, the dashes ( - - - ) represent the mean, and the solid (_____) represents the median.

For the lower $CGG_n$ allele, in most cases representative of a low FMR1 genotype/sub-genotype, values amongst the two groups were significantly different [Mann-Whiney U=(Mean Rank 83.37$_{low}$, 296.44$_{high}$; Z=-13.10; P=0.001)].

Similarly, the higher count $CGG_n$ allele, mostly representing high FMR1 genotypes/sub-genotypes, varied amongst the two groups (Mann-Whitney U=Mean Rank 231.18$_{low}$, 260.75$_{high}$; Z=-0.069; P=0.07) but failed to reach statistical significance (see FIGS. 7 and 8).

The most likely explanation for complete absence of the het-norm/high ovarian FMR1 sub-genotype, minimal presence of norm genotypes, and excessive presence of het-norm/low sub-genotypes in BRCA1/2-positive women is that BRCA1/2 mutations are embryo-lethal gene mutations for humans. A low ($CGG_{n<26}$) sub-genotype allele, however, appears to block embryo lethality of BRCA1/2. Such low sub-genotypes can be present in het-norm/low, hom-low/low and hom/high/low FMR1 sub-genotypes, combined, representing approximately 25 percent of all women (see FIG. 3).

Het sub-genotypes have been reasonably well defined in their respective ovarian functions. They, somewhat surprisingly, in women with infertility were also associated with risk towards autoimmunity. Hom sub-genotypes, because of low prevalence, are, however, not yet defined. Because of small numbers, they, in this study, also had to be collapsed into a single group. Hom patients may, therefore, contain functionally opposing, and, therefore balancing, sub-genotypes but final determinations await further studies.

Like the FMR1 gene in its genotypes and sub-genotypes, BRCA1/2 may be associated with premature diminished ovarian reserve. The gene, however, has never before been suspected of being embryo-lethal in humans.

Some prior evidence for embryo-lethality of BRCA1/2 exists, however: When in the mid-1990 first BRCA1/2 mouse models were developed, heterozygous mice did not express expected phenotypes. Therefore, homozygous models were developed, which proved embryo-lethal. Different mouse mutant for BRCA1/2, however, display great variability in phenotypes and in rescue of embryonic lethality on a p53-null background.

BRCA1/2 genetically interacts with the p53 pathway, which is, at least partially, believed to explain the so-called "BRCA paradox," with BRCA-deficient tumor cells rapidly proliferating, while BRCA-deficient embryos suffer from a proliferation defects. BRCA1 mutant embryos were partially rescued in a p53- or p21-deficient background, while BRCA2 knockout mice were less successfully rescued by absence of p53, suggesting that, in addition to p53, other factors contribute to the abnormal proliferation in BRCA1/2 deficient mouse embryos. In animal experiments, p53-nullizygousity, indeed, can rescue some BRCA1 mouse mutants but may only delay lethality.

Currently available data suggest that in humans the normal range for $CGG_n$ on the FMR1 gene is 26 to 34 repeats. The norm genotype of the FMR1 gene, with both alleles in normal range ($CGG_{n=26-34}$), likely, represented the original (ur-) FMR1 gene. Mutations may have then generated the het and hom genotypes, depending on whether only one or both alleles mutated outside normal range.

Under such a concept, mutations of $CGG_{n>34}$ generated high sub-genotypes through the gene's well-recognized ability to expand (12). The gene's so far largely uninvestigated ability to contract to $CGG_{n<26}$, resulted in low sub-genotypes, and this study demonstrates that it is responsible for the rescue of female embryos with BRCA1/2 mutations from lethality.

The here reported ability of the het-norm/low sub-genotype of FMR1 to help avoid BRCA1/2-associated embryo lethality to such a significant degree, adds to the rapidly increasing biological importance of the FMR1 gene. Until recently, FMR1 was, primarily, only known for neuro-psychiatric problems in association with traditional premutation and full mutation genotypes. The gene's only known not neuro-psychiatric disease association was, at premutation range ($CGG_{n=55-200}$), with premature ovarian failure (POF), now often given the acronym primary ovarian insufficiency (POI). It was this association that led us to search for a potentially associated ovarian function effect of the FMR1 gene.

Aside from effects on ovarian reserve and, consequently, ovarian aging patterns, this led us to discover the association of the het-norm/low sub-genotype with an, at young age, rapidly follicle depleting polycystic ovary-like phenotype, and with substantially decreased pregnancy chances with infertility treatments.

Somewhat more surprising, we, however, also noted a close association of het-norm low with risk towards autoimmunity, while het-norm/high demonstrated strongly protective effects. This observation for the first time suggested opposing clinical effects of the two het sub-genotypes of the FMR1 gene, and did so outside of historically known neuropsychiatric effects and newly discovered ovarian/fertility effects of the gene. Opposing clinical effects of het-norm/low and het-norm/high genotypes should, however, not surprise since $CGG_{n=30}$, the median of the gene's normal range, has been described as switching point between positive and negative message.

Especially since autoimmunity demonstrates a disease preponderance in women over men, these findings significantly enhance the physiologic and clinical importance of the FMR1 gene. A potential autoimmune function of the FMR1 gene, however, dwarfs in comparison to what here reported data suggest: They imply that $CGG_{n<26}$, represented by het-norm/low, and possibly low hom sub-genotypes, biologically and clinically may be of far greater important than expanded $CGG_{n>34}$ ranges, represented by het-norm/high and, possibly, hom-high genotypes. The latter, of course, include traditional premutation and full mutation genotypes of FMR1, the latter associated with the fragile X syndrome. Suffice it to say; low ($CGG_{n<26}$), in contrast to high $CGG_n$ counts ($CGG_{n>36}$), have so far, largely escaped attention, even though $CGG_{n=30}$ has been described as switching point for the FMR1 gene's message.

The het-norm/low sub-genotype of FMR1, thus, successfully combats embryo lethality of BRCA1/2 mutations; the biological/clinical cost for survival, however, appears steep because it increases autoimmunity and BRCA1/2 mediated cancer risks.

FMR1, considering it maps to the 5' untranslated exon 1 on the X chromosome at Xq27.3, a region now widely considered associated with autoimmune risks, appears to represent crossroads between autoimmunity and reproduction. It now appears that FMR1 is located at triple crossroads of autoimmunity, cancer and reproduction.

Lifetime risk for breast cancer in the U.S., according to most recent National Cancer Institute data, is 1 per 8.2 women for a 12.2 percent risk per woman. In presence of BRCA1/2 mutations, the risk increases approximately five-fold to ca. 60 percent. BRCA1/2 mutations, thus, account for 5-10 percent of all breast cancers.

Lifetime ovarian cancer risk in the U.S. is ca. 1.4 percent but this risk, in presence of BRCA1/2 mutations, is increased 10.7 to 28.6-fold to a 15 to 40 percent range. Overall, BRCA1/2, thus, accounts for 10 to 15 percent of all ovarian cancer risk.

While breast and ovarian cancers are the most frequent BRCA1/2 associated malignancies, other cancers also demonstrate increased prevalence. In association with BRCA1, those include, for example, malignancies of the uterine cervix and corpus, pancreas and colon; in association with BRCA2, they include, for example, cancers of pancreas, stomach, gallbladder, bile ducts and malignant melanoma.

Genetic cancer screening for BRCA1/2 mutations is now generally restricted to high risk families for breast and ovarian cancer. Avoidance of BRCA1/2 embryo lethality only in presence of the FMR1 sub-genotype het-norm/low, however, suggests that het-norm/low women, due to their substantial BRCA1/2 carrier status, should be at significantly increased risk for all BRCA1/2 associated cancers. In contrast, the reported association between BRCA1 and prematurely diminished ovarian reserve likely reflects the high het-norm/low prevalence in such patients.

As here again demonstrated, in excess of 20 percent of women in a general population can be expected to exhibit the het-norm/low sub-genotype, and ca. 25 percent, combined, a low ($CGG_{n<26}$) het or hom allele. These women, therefore, have to be considered at increased risk for BRCA1/2-associated cancers, autoimmunity and infertility.

The estimated population frequency for BRCA1/2 mutations (0.024 to 0.04%) in recessive and polygenic models, respectively, causes 5 to 10 percent of all breast cancer risk and 10 to 15 percent of all ovarian cancer risk. Extrapolating, the het-norm/low FMR1 sub-genotype, representing approximately 78.8 percent of BRCA1/2 patients, spread over only ca. a quarter of all women, would reflect 3.95 to 7.9 percent of all breast and 7.9 to 11.9 percent of ovarian cancer risk, concentrated in only approximately a quarter of the female population. Therefore, approximately 75 percent of the female population could, thus, be assured of very low BRCA1/2 related cancer risks, and ca. 15 to 16 percent of women with het-norm/high sub-genotype of practically no risk at all. The impact from these findings on current breast cancer screening guidelines may, therefore, be significant.

Distributions of FMR1 genotypes and sub-genotypes as well as prevalence of BRCA1/2 mutations, of course, vary in different races/ethnicities. Interestingly, so do female cancers, autoimmunity and female infertility prevalence. These observations may be associated.

For women, the FMR1 gene, therefore, emerges as a potentially very important screening tool for risk towards a multitude of serious potential medical problems, including infertility, autoimmunity and cancer risks.

Based on the observation that BRCA in normal cells induces growth arrest, while promoting tumor formation in BRCA mutation carriers, some have pointed at the likely presence of secondary suppressor mutations, which may overcome BRCA-associated arrests during BRCA-associated tumorigenesis. With the FMR1 gene at crossroads of reproductive, immunologic and cancer-associated effects, it is tempting to hypothesize about just such, each other opposing, functions for the two het sub-genotypes of FMR1, het-norm/high and het-norm/low.

The here investigated patient populations are European and American, and, therefore, may reflect different genetic diversities. Furthermore, their retroactive evaluations may have resulted in selection biases. Assay performance in different laboratories may have resulted in divergent results between study groups. Similarities in FMR1 genotype and sub-genotype distribution between Austrian and U.S. control groups, however, practically rule out significant statistical impact from laboratory variability.

Statistical clarity of the here reported results, therefore, strongly supports reported assertions, which appear statistically robust. Combined, the results suggest major new biological and clinical importance for FMR1 and BRCA1/2 mutations.

While the foregoing written description of the invention enables one of ordinary skill to make and use what is considered presently to be the best mode thereof, those of ordinary skill will understand and appreciate the existence of variations, combinations, and equivalents of the specific exemplary embodiments thereof. The invention is therefore to be limited not by the exemplary embodiments herein, but by all embodiments within the scope and spirit of the appended claims.

What is claimed is:

1. A method of treating a human female to reduce the risk or spread of breast or ovarian cancer, comprising:
   isolating an FMR1 gene from the human female;
   measuring the number of triple CGG repeats on each allele of the isolated FMR1 gene by using an assay;
   determining that the number of triple CGG repeats on at least one of the alleles of the isolated FMR1 gene is less than 26; and
   administering an FMR1 inhibitor to the human female to block expression of the FMR1 gene.

2. A method for treating a human female to reduce the risk or spread of breast or ovarian cancer comprising:
   isolating at least one of the human female's BRCA1 gene and BRCA2 gene;
   analyzing at least one of the BRCA1 and BRCA2 genes for mutations;
   determining that a mutation exists on at least one of the BRCA1 and BRCA2 genes; and
   administering an FMR1 inhibitor.

3. The method according to claim 1 wherein the FMR1 inhibitor comprises siRNA.

4. The method according to claim 1 wherein the FMR1 inhibitor comprises a pharmaceutical agent based on the three-dimensional structure of FMR1 obtained by at least one of X-ray Crystallography and Nuclear Magnetic Resonance (NMR) data.

5. The method according to claim 1 wherein administering the FMR1 inhibitor comprises using gene therapy to overexpress a ZF5 transcription factor.

6. The method according to claim 1 wherein administering the FMR1 inhibitor comprises using gene therapy to overexpress a USF2 transcription factor.

7. The method according to claim 1 wherein administering the FMR1 inhibitor comprises using gene therapy to overexpress CGGBP (CGG triplet binding protein 1).

8. The method according to claim 1 wherein administering the FMR1 inhibitor comprises using RNAi to downregulate an AP2-α transcription factor.

9. The method according to claim 1 wherein administering the FMR1 inhibitor comprises regulation of at least one transcription factor selected from the group consisting of NRF1, SP1, SP3, and USF1.

10. A method for treating a human female to reduce the risk or spread of breast or ovarian cancer comprising:
    isolating at least one of the human female's BRCA1 gene and BRCA2 gene;
    analyzing at least one of the BRCA1 and BRCA2 genes for mutations;
    isolating an FMR1 gene from the human female;
    measuring the number of triple CGG repeats on each allele of the isolated FMR1 gene by using an assay; and
    administering an FMR1 inhibitor when at least one of the BRCA1 or BRCA2 genes has a mutation and the number of triple CGG repeats on at least one of the alleles of the isolated FMR1 gene is less than 26.

11. The method according to claim 2 wherein the FMR1 inhibitor comprises siRNA.

12. The method according to claim 2 wherein the FMR1 inhibitor comprises a pharmaceutical agent based on the three-dimensional structure of FMR1 obtained by at least one of X-ray Crystallography and Nuclear Magnetic Resonance (NMR) data.

13. The method according to claim 2 wherein administering the FMR1 inhibitor comprises using gene therapy to overexpress a ZF5 transcription factor.

14. The method according to claim 2 wherein administering the FMR1 inhibitor comprises using gene therapy to overexpress a USF2 transcription factor.

15. The method according to claim 2 wherein administering the FMR1 inhibitor comprises using gene therapy to overexpress CGGBP (CGG triplet binding protein 1).

16. The method according to claim 2 wherein administering the FMR1 inhibitor comprises using RNAi to downregulate an AP2-α transcription factor.

17. The method according to claim 2 wherein administering the FMR1 inhibitor comprises regulation of at least one transcription factor selected from the group consisting of NRF1, SP1, SP3, and USF1.

18. The method according to claim 10 wherein the FMR1 inhibitor comprises siRNA.

19. The method according to claim 10 wherein the FMR1 inhibitor comprises a pharmaceutical agent based on the three-dimensional structure of FMR1 obtained by at least one of X-ray Crystallography and Nuclear Magnetic Resonance (NMR) data.

20. The method according to claim 10 wherein administering the FMR1 inhibitor comprises using gene therapy to overexpress a ZF5 transcription factor.

21. The method according to claim 10 wherein administering the FMR1 inhibitor comprises using gene therapy to overexpress a USF2 transcription factor.

22. The method according to claim 10 wherein administering the FMR1 inhibitor comprises using gene therapy to overexpress CGGBP (CGG triplet binding protein 1).

23. The method according to claim 10 wherein administering the FMR1 inhibitor comprises using RNAi to downregulate an AP2-α transcription factor.

24. The method according to claim 10 wherein administering the FMR1 inhibitor comprises regulation of at least one transcription factor selected from the group consisting of NRF1, SP1, SP3, and USF1.

* * * * *